(12) United States Patent
Yamada et al.

(10) Patent No.: US 8,691,398 B2
(45) Date of Patent: *Apr. 8, 2014

(54) 4-AMINOFLUORENE COMPOUND AND ORGANIC LIGHT EMITTING DEVICE

(75) Inventors: Naoki Yamada, Inagi (JP); Chika Negishi, Yokosuka (JP); Keiji Okinaka, Kawasaki (JP); Minako Nakasu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 648 days.

This patent is subject to a terminal disclaimer.

(21) Appl. No.: 12/158,117

(22) PCT Filed: Dec. 15, 2006

(86) PCT No.: PCT/JP2006/325668
§ 371 (c)(1),
(2), (4) Date: Oct. 26, 2009

(87) PCT Pub. No.: WO2007/072952
PCT Pub. Date: Jun. 28, 2007

(65) Prior Publication Data
US 2010/0033081 A1    Feb. 11, 2010

(30) Foreign Application Priority Data

Dec. 20, 2005 (JP) ................. 2005-366558
Jun. 15, 2006 (JP) ................. 2006-166200
Nov. 22, 2006 (JP) ................. 2006-315716

(51) Int. Cl.
*H01L 51/54* (2006.01)
*C07C 211/44* (2006.01)
(52) U.S. Cl.
USPC ........... 428/690; 428/917; 313/504; 313/506; 564/427

(58) Field of Classification Search
None
See application file for complete search history.

(56) References Cited

U.S. PATENT DOCUMENTS

| 5,061,569 A | 10/1991 | VanSlyke et al. | ............ 428/457 |
| 6,858,325 B2 * | 2/2005 | Senoo et al. | ................. 428/690 |

(Continued)

FOREIGN PATENT DOCUMENTS

| JP | 03-078756 | 4/1991 |
| JP | 04-220995 | 8/1992 |

(Continued)

OTHER PUBLICATIONS

Machine translation for JP 2003-201472, which was published Jul. 2003.*

(Continued)

*Primary Examiner* — Dawn L Garrett
(74) *Attorney, Agent, or Firm* — Fitzpatrick, Cella, Harper & Scinto

(57) ABSTRACT

To provide a compound excellent in light emitting properties and an organic light emitting device having the compound. The compound is a 4-aminofluorene compound represented by the following general formula (1):

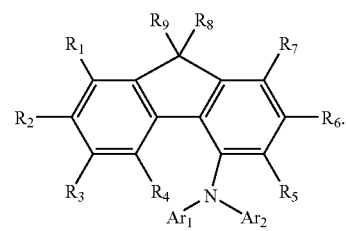

(1)

14 Claims, 2 Drawing Sheets

(56) References Cited

U.S. PATENT DOCUMENTS

| | | | |
|---|---|---|---|
| 7,241,513 B2 | 7/2007 | Suzuki et al. | 428/690 |
| 7,338,721 B2 | 3/2008 | Suzuki et al. | 428/690 |
| 7,691,492 B2 * | 4/2010 | Yamada et al. | 428/690 |
| 7,998,597 B2 * | 8/2011 | Saitoh et al. | 428/690 |
| 2003/0068524 A1 * | 4/2003 | Hatwar | 428/690 |
| 2004/0028944 A1 | 2/2004 | Mori et al. | 428/691 |
| 2004/0189190 A1 | 9/2004 | Suzuri et al. | 313/504 |
| 2006/0166034 A1 | 7/2006 | Saitoh et al. | 428/690 |
| 2007/0228941 A1 | 10/2007 | Abe et al. | 313/504 |
| 2007/0287029 A1 * | 12/2007 | Kawamura et al. | 428/704 |

FOREIGN PATENT DOCUMENTS

| | | |
|---|---|---|
| JP | 05-009471 | 1/1993 |
| JP | 05-234681 | 9/1993 |
| JP | 05-303221 | 11/1993 |
| JP | 11-144875 | 5/1999 |
| JP | 11-224779 | 8/1999 |
| JP | 11-288783 | 10/1999 |
| JP | 2001-039933 | 2/2001 |
| JP | 2002-324678 | 11/2002 |
| JP | 2003-201472 * | 7/2003 |
| JP | 2004-139819 | 5/2004 |
| JP | 2004-231547 | 8/2004 |
| JP | 2004-311424 | 11/2004 |
| JP | 2005-272803 | 10/2005 |
| JP | 2005-272805 | 10/2005 |
| WO | WO 02/30159 A1 | 4/2002 |

OTHER PUBLICATIONS

Kajigaeshi et al., "Selective Preparation of Fluorene Derivatives Using the *t*-Butyl Function as a Positional Protective Group," *Bull. Chem. Soc. Jpn.*, vol. 59, 97-103 (1986).

Supplementary European Search Report dated Oct. 8, 2009 for European Application No. 06 83 5131 (2 pages).

* cited by examiner

4-AMINOFLUORENE COMPOUND AND ORGANIC LIGHT EMITTING DEVICE

TECHNICAL FIELD

The present invention relates to a novel 4-aminofluorene compound and an organic light emitting device.

BACKGROUND ART

An organic light emitting device is a device which includes a thin film which contains a fluorescent organic compound or a phosphorescent organic compound and is interposed between an anode and a cathode.

Further, a hole and an electron are injected from the respective electrodes, whereby an exciton of the fluorescent compound or the phosphorescent compound is generated. Light is radiated upon return of the exciton to its ground state.

The recent progress of an organic light emitting device is significant, and the device suggests its potential to find use in a wide variety of applications because of the following reasons. The device shows a high luminance at a low applied voltage. In addition, the device has a variety of light emission wavelengths. Furthermore, the device can be a thin, light-weight light emitting device with high-speed responsiveness.

However, at present, an optical output with additionally high luminance, or additionally high conversion efficiency has been needed. In addition, the organic light emitting device still has many problems in terms of durability. For example, the device changes over time owing to long-term use, and deteriorates owing to an atmospheric gas containing oxygen, humidity, or the like.

Further, in the case where it is assumed that the device is applied to, for example, a full-color display, the device must emit blue light, green light, and red light each having good color purity. However, problems concerning the color purity of each of the blue light, the green light, and the red light have not been sufficiently solved yet.

In addition, examples of a material and an organic light emitting device each using a fluorene compound are disclosed in Japanese Patent Application Laid-Open Nos. H11-144875, H11-224779, H11-288783 and 2001-39933. However, each of the devices described in those documents has low external quantum efficiency and an insufficient duration lifetime.

In addition, examples of a material and an organic light emitting device each using an aromatic tertiary amine derivative are disclosed Japanese Patent Application Laid-Open Nos. H04-220995, 2002-324678, H05-234681 and H05-009471.

DISCLOSURE OF THE INVENTION

An object of the present invention is to provide a novel 4-aminofluorene compound.

Another object of the present invention is to provide an organic light emitting device using a 4-aminofluorene compound and having extremely high efficiency and an optical output with high luminance. Another object of the present invention is to provide an organic light emitting device having extremely high durability.

Another object of the present invention is to provide an organic light emitting device that can be easily produced at a relatively low cost.

That is, the present invention provides:

1) a 4-aminofluorene compound represented by the following general formula (1):

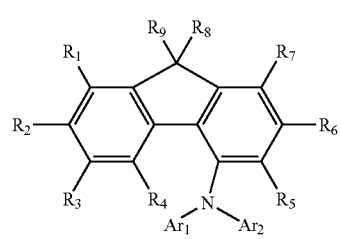

wherein $Ar_1$ represents a substituted or unsubstituted fluorene group to be bonded to 2- or 4-position, $Ar_2$ represents a substituted or unsubstituted aryl group, or a substituted or unsubstituted heterocyclic group, and $R_1$ to $R_9$ each represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen group, and may be identical to or different from each other, or may be bonded to each other to form a ring;

2) a 4-aminofluorene compound according to Paragraph (1), in which, in the general formula (1), $Ar_1$ represents a substituted or unsubstituted fluorene group to be bonded to 4-position, and $Ar_2$ represents a substituted or unsubstituted fluorene group;

3) a 4-aminofluorene compound according to Paragraph (1), in which, in the general formula (1), $Ar_1$ represents a substituted or unsubstituted fluorene group to be bonded to 4-position, and $Ar_2$ represents a substituted or unsubstituted fluorene group;

4) an organic light emitting device including:
a pair of electrodes composed of an anode and a cathode; and
a layer containing an organic compound and being interposed between the pair of electrodes,
wherein the layer containing an organic compound contains at least one kind of the compound according to Paragraph 1);

5) an organic light emitting device including:
a pair of electrodes composed of an anode and a cathode; and
a layer containing an organic compound and being interposed between the pair of electrodes,
wherein the layer containing an organic compound is a hole transport region containing at least one kind of the compound according to Paragraph 1);

6) an organic light emitting device including:
a pair of electrodes composed of an anode and a cathode; and
a layer containing an organic compound and being interposed between the pair of electrodes,
wherein the layer containing an organic compound is a light emitting layer containing at least one kind of the compound according to Paragraph 1);

7) an organic light emitting device including:
a pair of electrodes composed of an anode and a cathode; and
plural layers each containing an organic compound, the plural layers being interposed between the pair of electrodes, wherein:
the plural layers comprise
a light emitting layer,
a second hole transport layer adjacent to the light emitting layer on the anode side of the light emitting layer, and a first hole transport layer adjacent to the second hole transport layer on the anode side of the second hole transport layer, the first hole transport layer containing at least one kind of a compound having an amine; and the second hole transport layer contains at least one kind of a tertiary amine compound having one nitrogen atom;

8) an organic light emitting device according to Paragraph 7), in which the first hole transport layer contains at least one kind of a tertiary amine compound having one nitrogen atom;

9) an organic light emitting device according to Paragraph 7), in which the first hole transport layer contains at least one kind of a non-cyclic tertiary amine compound having one nitrogen atom;

10) an organic light emitting device according to Paragraph (7), in which the second hole transport layer contains at least one kind of a non-cyclic tertiary amine compound having one nitrogen atom;

11) an organic light emitting device according to Paragraph 7), in which the compound having an amine comprises a 4-aminofluorene compound represented by the following general formula (1):

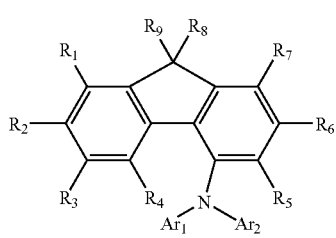

(1)

wherein $Ar_1$ represents a substituted or unsubstituted fluorene group to be bonded to 2- or 4-position, $Ar_2$ represents a substituted or unsubstituted aryl group, or a substituted or unsubstituted heterocyclic group, and $R_1$ to $R_9$ each represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen group, and may be identical to or different from each other, or may be bonded to each other to form a ring;

12) an organic light emitting device according to Paragraph 7), in which the second hole transport layer contains at least one kind of a 4-aminofluorene compound represented by the following general formula (1):

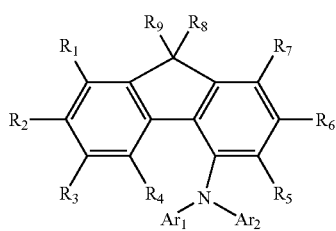

(1)

wherein $Ar_1$ represents a substituted or unsubstituted fluorene group to be bonded to 2- or 4-position, $Ar_2$ represents a substituted or unsubstituted aryl group, or a substituted or unsubstituted heterocyclic group, and $R_1$ to $R_9$ each represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen group, and may be identical to or different from each other, or may be bonded to each other to form a ring;

13) an organic light emitting device according to Paragraph 7), in which a band gap of the tertiary amine compound having one nitrogen atom and present in the second hole transport layer is wider than a band gap of a compound a content of which in the light emitting layer is highest; and 14) an organic light emitting device according to Paragraph 7), in which an ionization potential Ip1 of a compound a content of which in the first hole transport layer is highest, an ionization potential Ip2 of a compound a content of which in the second hole transport layer is highest, and an ionization potential Ip3 of a compound a content of which in the light emitting layer is highest satisfy a relationship of $Ip1<Ip2<Ip3$.

The 4-aminofluorene compound represented by the general formula (1) of the present invention has excellent light emitting properties. In addition, an organic light emitting device using the 4-aminofluorene compound emits light with high efficiency at a low applied voltage. In addition, the device provides excellent durability.

BEST MODE FOR CARRYING OUT THE INVENTION

Figure 1:
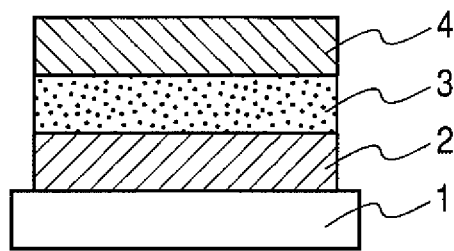
FIG. 1 is a sectional view showing an example of an organic light emitting device in the present invention.

Specific examples of the substituents of the compound in the general formula (1) will be shown below.

As the alkyl group, there may be given a methyl group, an ethyl group, an n-propyl group, an isopropyl group, an n-butyl group, a tert-butyl group, a sec-butyl group, an octyl group, a 1-adamantyl group, a 2-adamantyl group, and the like.

As the aralkyl group, there may be given a benzyl group, a phenethyl group, and the like.

Examples of the aryl group include a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, and a fluorenyl group.

As the heterocyclic group, there may be given a thienyl group, a pyrrolyl group, a pyridyl group, an oxazolyl group, an oxadiazolyl group, a thiazolyl group, a thiadiazolyl group, a terthienyl group, a carbazolyl group, an acridinyl group, a phenanthrolyl group, and the like.

As the halogen atom, there may be given fluorene, chlorine, bromine, iodine, and the like.

Examples of substituents which the above-mentioned substituents may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; and halogen atoms such as a cyano group, fluorene, chlorine, bromine, and iodine.

The fluorene compound of the present invention can be synthesized by using a 4-aminofluorene derivative or a 4-bromofluorene derivative as a raw material. In addition, each of those raw materials can be synthesized with reference to Bull. Chem. Soc. Jpn., 59, 97-103 (1986).

The 4-aminofluorene compound represented by the general formula (1) can be used as a material for an organic light emitting device.

In the organic light emitting device, the 4-aminofluorene compound represented by the general formula (1) can be used in each of a hole transport layer and a light emitting layer. As a result, a device having high luminous efficiency and a long lifetime can be obtained.

In addition, when the fluorene compound represented by the general formula (1) is used in a light emitting layer, the compound can be used alone in the light emitting layer, and can be used as a host material for each of a dopant (guest) material, a fluorescent material, and a phosphorescent material. As a result, a device having high color purity, high luminous efficiency, and a long lifetime can be obtained.

When 4-position of the fluorene group of the 4-aminofluorene compound represented by the general formula (1) is substituted by an amino group, an entire molecule can be designed in a non-planar fashion. Accordingly, as shown in Examples 12 to 30 and Comparative Examples, the 4-aminofluorene compound provides a molecule having higher amorphous property than that of a molecule provided by a 2-aminofluorene compound, so heat stability is high, and a device having a long lifetime can be obtained. In addition, the case where each of substituents on the amino group by which 4-position of the fluorene group is substituted ($Ar_1$ and $Ar_2$ in the general formula (1)) is a fluorene group is more preferable because heat stability is additionally improved. The case where the above substituent $Ar_1$ on the amino group is a fluorene group and is bonded to the nitrogen atom on the amino group at 4-position of the fluorene group is still more preferable because the non-planarity of an entire molecule is improved, heat stability is additionally improved, and a device having a long lifetime can be obtained.

In addition, non-planar molecular design provides a hole transport material having a wide band gap, so the injection of an electron from a light emitting layer to a hole transport layer can be inhibited, and the transfer of the energy of an exciton generated in the light emitting layer to the hole transport layer can be inhibited. Accordingly, a device having high efficiency can be obtained.

The introduction of a substituent to a fluorene group or an amino group enables the easy adjustment of an HOMO/LUMO level. Accordingly, a molecule of a hole transport material can be easily designed while a balance between the injection and transport of a hole from an anode to a light emitting layer is taken into consideration. Further, the luminescent color of a luminescent material can be converted to a blue color, a green color, or any color having a longer wavelength.

In addition, an organic light emitting device including: a pair of electrodes composed of an anode and a cathode; and a layer containing an organic compound and being interposed between the pair of electrodes may include a layer containing, for example, copper phthalocyanine (CuPc) or carbon fluoride (CFx) from which an improvement in property with which a hole is injected from the anode can be expected.

The present invention has been achieved by molecular design based on such discussion as described above.

Hereinafter, the present invention will be described in detail.

Specific examples of the compound in the above general formula (1) are shown below. However, the present invention is not limited to these examples. In addition, any one of the combinations of Exemplified Compounds 1 to 69 may be used as a combination of $Ar_1$ and $Ar_2$.

| Compound No. | Fluorene group |
|---|---|
| 1 | |
| 2 | |
| 3 | |

-continued
4 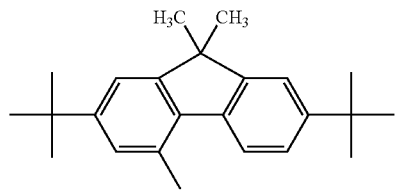 [SMILES: Cc1cc(C(C)(C)C)cc2c1-c1ccc(C(C)(C)C)cc1C2(C)C]
5 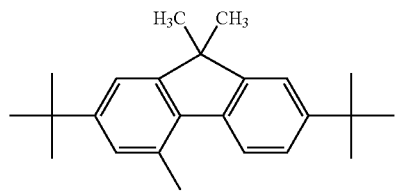
6 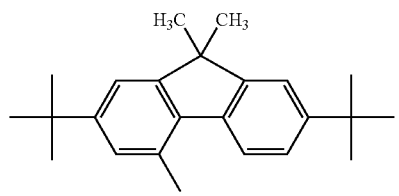 [SMILES: Cc1cc(C(C)(C)C)cc2c1-c1ccc(C(C)(C)C)cc1C2(C)C]
7 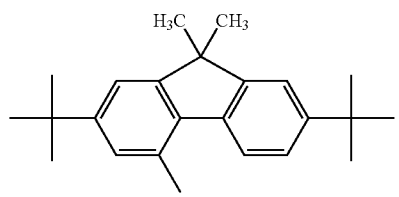 [SMILES: Cc1cc(C(C)(C)C)cc2c1-c1ccc(C(C)(C)C)cc1C2(C)C]
8 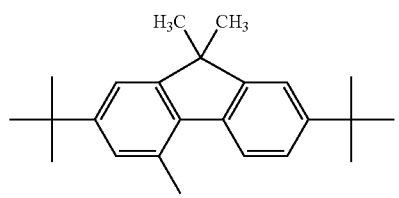
9 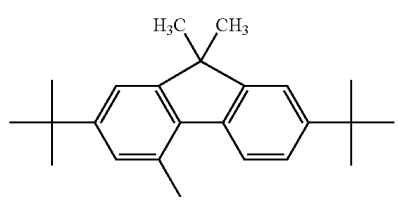 [SMILES: Cc1cc(C(C)(C)C)cc2c1-c1ccc(C(C)(C)C)cc1C2(C)C]
10 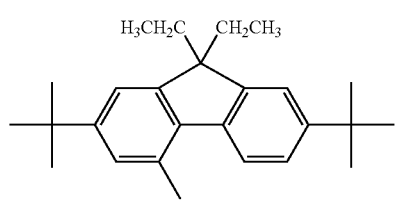
11 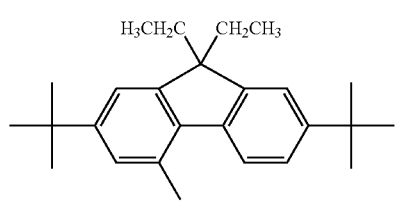

-continued
12 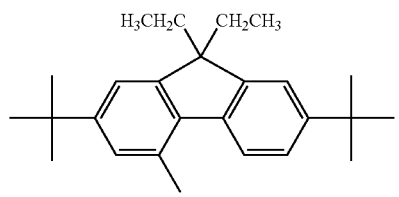
13 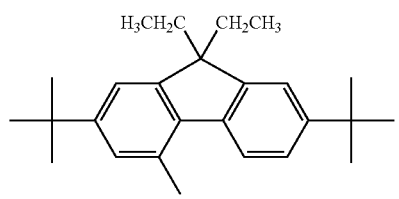
14 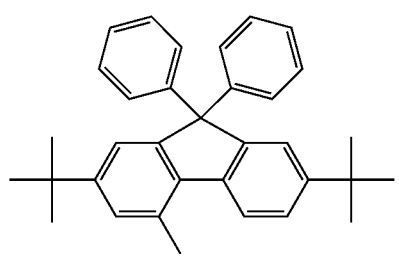 [SMILES: Cc1cc(C(C)(C)C)cc2c1-c1ccc(C(C)(C)C)cc1C2(c1ccccc1)c1ccccc1]
15 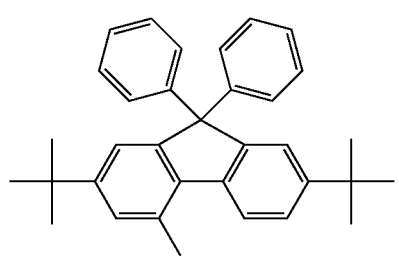 [SMILES: Cc1cc(C(C)(C)C)cc2c1-c1ccc(C(C)(C)C)cc1C2(c1ccccc1)c1ccccc1]
16 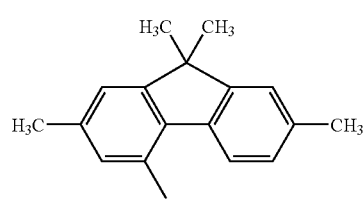
17 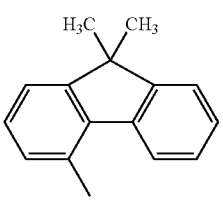 [SMILES: Cc1cccc2c1-c1ccccc1C2(C)C]
18 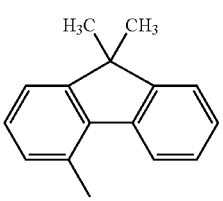 [SMILES: Cc1cccc2c1-c1ccccc1C2(C)C]

-continued
19
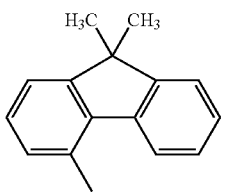 [SMILES: Cc1cccc2c1-c1ccccc1C2(C)C]
20
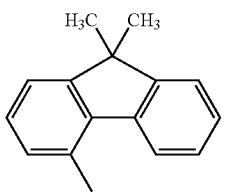 [SMILES: Cc1cccc2c1-c1ccccc1C2(C)C]
21
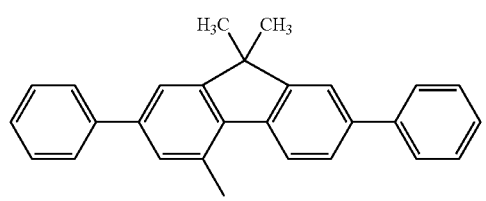
22
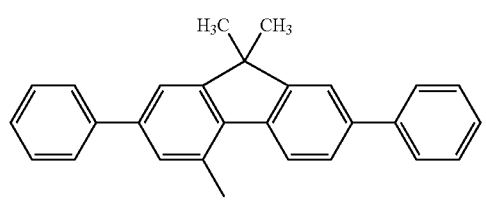 [SMILES: Cc1cc(-c2ccccc2)cc2c1-c1ccc(-c3ccccc3)cc1C2(C)C]
23
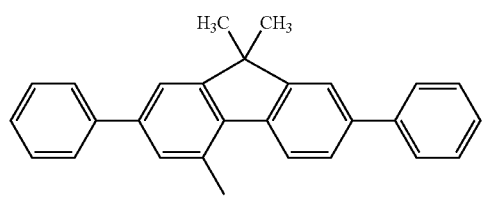 [SMILES: Cc1cc(-c2ccccc2)cc2c1-c1ccc(-c3ccccc3)cc1C2(C)C]
24
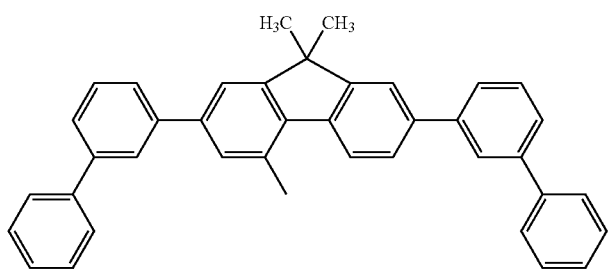 [SMILES: Cc1cc(-c2cccc(-c3ccccc3)c2)cc2c1-c1ccc(-c3cccc(-c4ccccc4)c3)cc1C2(C)C]
25
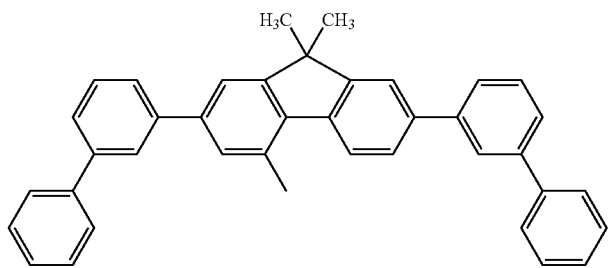 [SMILES: Cc1cc(-c2cccc(-c3ccccc3)c2)cc2c1-c1ccc(-c3cccc(-c4ccccc4)c3)cc1C2(C)C]

26 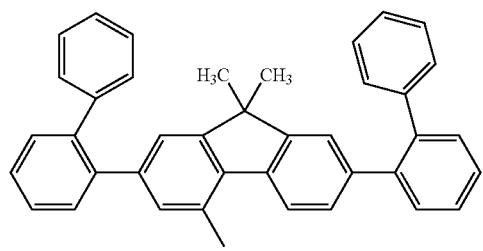 [SMILES: Cc1cc(-c2ccccc2-c2ccccc2)cc2c1-c1ccc(-c3ccccc3-c3ccccc3)cc1C2(C)C]
27 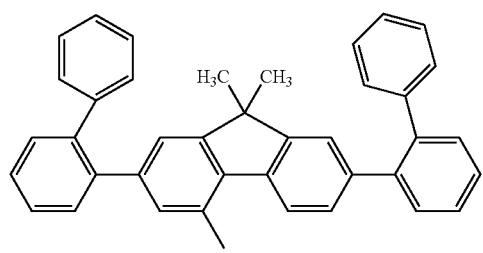 [SMILES: Cc1cc(-c2ccccc2-c2ccccc2)cc2c1-c1ccc(-c3ccccc3-c3ccccc3)cc1C2(C)C]
28 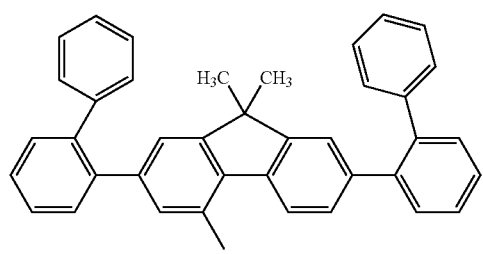 [SMILES: Cc1cc(-c2ccccc2-c2ccccc2)cc2c1-c1ccc(-c3ccccc3-c3ccccc3)cc1C2(C)C]
29 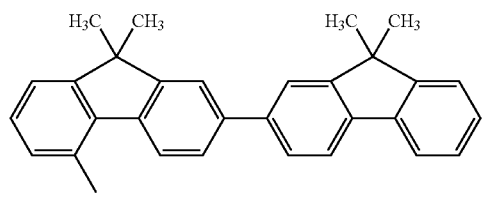 [SMILES: Cc1cccc2c1-c1ccc(-c3ccc4c(c3)C(C)(C)c3ccccc3-4)cc1C2(C)C]
30 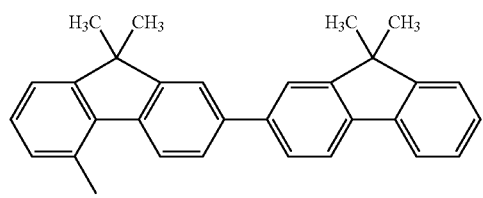 [SMILES: Cc1cccc2c1-c1ccc(-c3ccc4c(c3)C(C)(C)c3ccccc3-4)cc1C2(C)C]
31 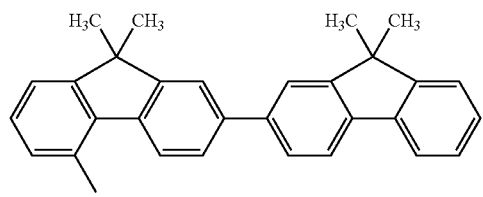 [SMILES: Cc1cccc2c1-c1ccc(-c3ccc4c(c3)C(C)(C)c3ccccc3-4)cc1C2(C)C]
32 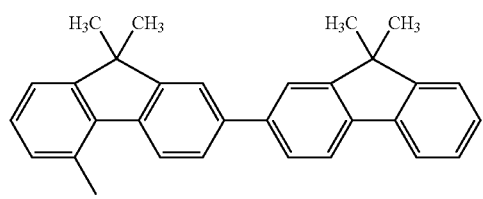 [SMILES: Cc1cccc2c1-c1ccc(-c3ccc4c(c3)C(C)(C)c3ccccc3-4)cc1C2(C)C]

-continued
| | |
|---|---|
| 33 | 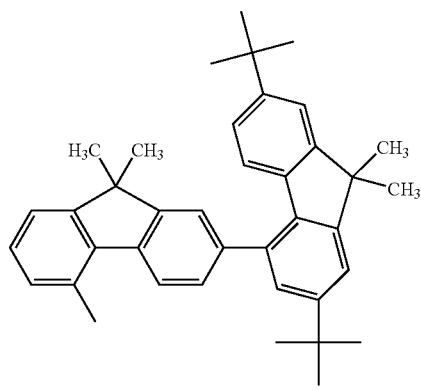 [SMILES: Cc1cccc2c1-c1ccc(-c3cc(C(C)(C)C)cc4c3-c3ccc(C(C)(C)C)cc3C4(C)C)cc1C2(C)C] |
| 34 | 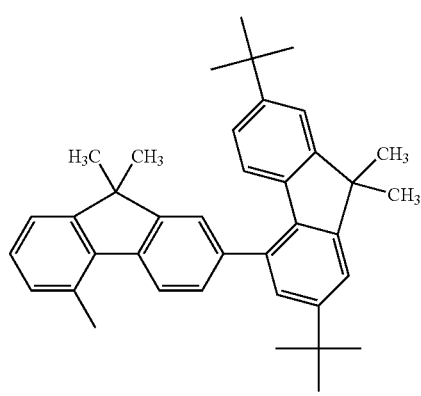 [SMILES: Cc1cccc2c1-c1ccc(-c3cc(C(C)(C)C)cc4c3-c3ccc(C(C)(C)C)cc3C4(C)C)cc1C2(C)C] |
| 35 | 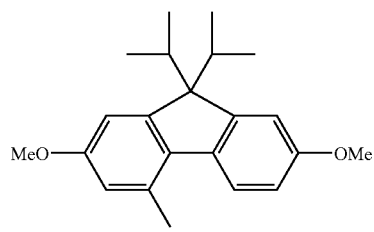 [SMILES: COc1ccc2c(c1)C(C(C)C)(C(C)C)c1cc(OC)cc(C)c1-2] |
| 36 | 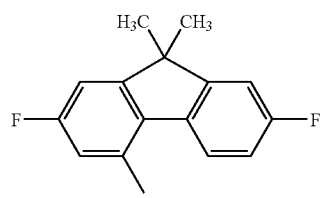 |
| 37 | 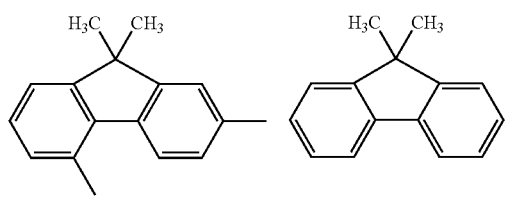 |
| 38 | 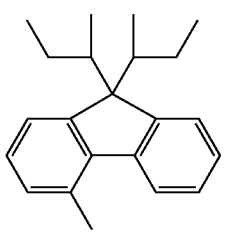 [SMILES: CCC(C)C1(C(C)CC)c2ccccc2-c2c(C)cccc21] |

-continued
39 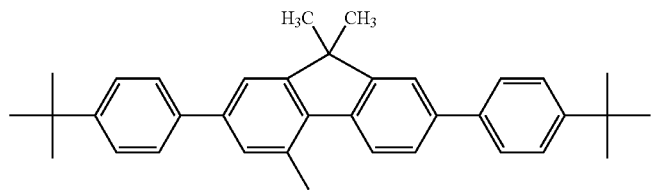 [SMILES: Cc1cc(-c2ccc(C(C)(C)C)cc2)cc2c1-c1ccc(-c3ccc(C(C)(C)C)cc3)cc1C2(C)C]
40 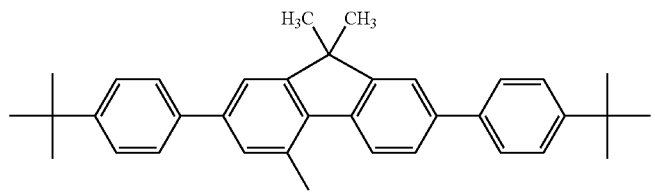 [SMILES: Cc1cc(-c2ccc(C(C)(C)C)cc2)cc2c1-c1ccc(-c3ccc(C(C)(C)C)cc3)cc1C2(C)C]
41 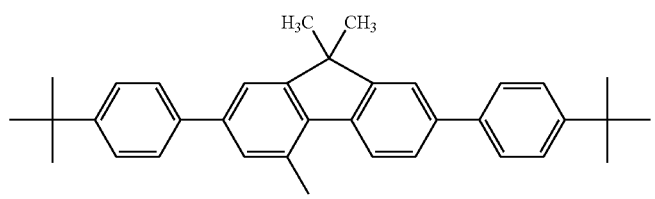 [SMILES: Cc1cc(-c2ccc(C(C)(C)C)cc2)cc2c1-c1ccc(-c3ccc(C(C)(C)C)cc3)cc1C2(C)C]
42 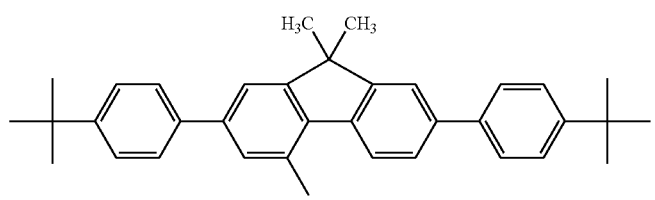 [SMILES: Cc1cc(-c2ccc(C(C)(C)C)cc2)cc2c1-c1ccc(-c3ccc(C(C)(C)C)cc3)cc1C2(C)C]
43 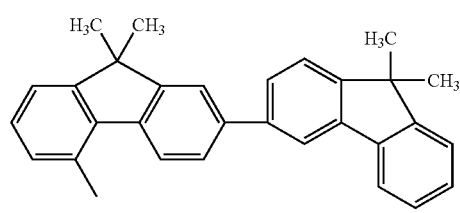 [SMILES: Cc1cccc2c1-c1ccc(-c3ccc4c(c3)-c3ccccc3C4(C)C)cc1C2(C)C]
44 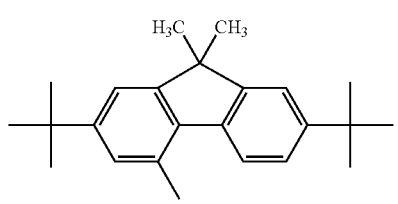
45 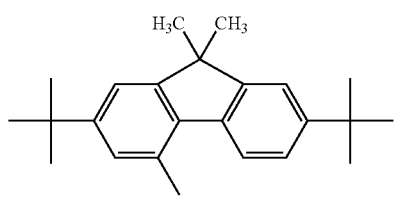 [SMILES: Cc1cc(C(C)(C)C)cc2c1-c1ccc(C(C)(C)C)cc1C2(C)C]
46 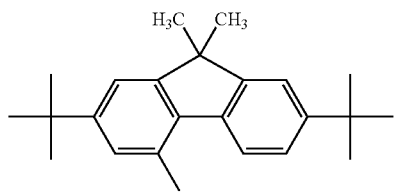

-continued
47 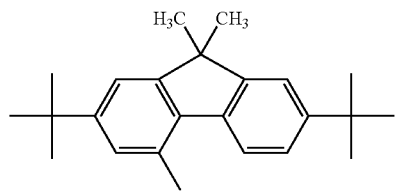 [SMILES: Cc1cc(C(C)(C)C)cc2c1-c1ccc(C(C)(C)C)cc1C2(C)C]
48 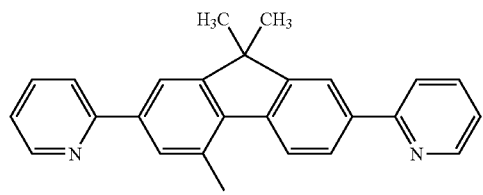
49 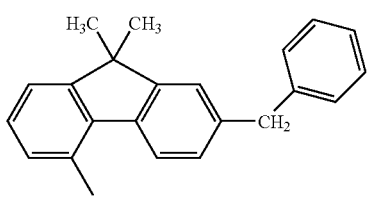 [SMILES: Cc1cccc2c1-c1ccc(Cc3ccccc3)cc1C2(C)C]
50 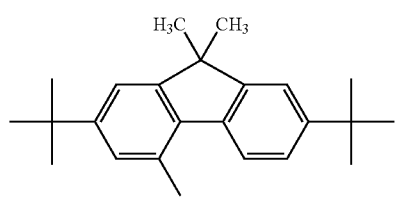 [SMILES: Cc1cc(C(C)(C)C)cc2c1-c1ccc(C(C)(C)C)cc1C2(C)C]
51 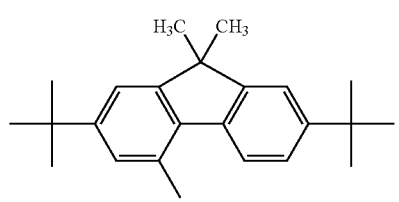 [SMILES: Cc1cc(C(C)(C)C)cc2c1-c1ccc(C(C)(C)C)cc1C2(C)C]
52 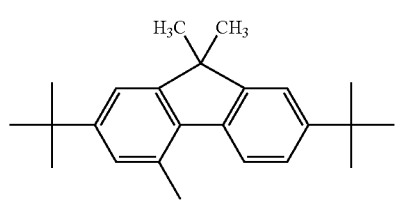 [SMILES: Cc1cc(C(C)(C)C)cc2c1-c1ccc(C(C)(C)C)cc1C2(C)C]
53 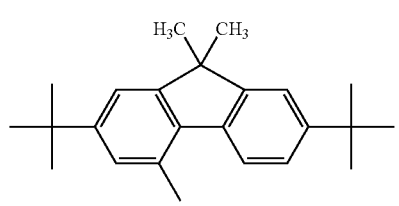
54 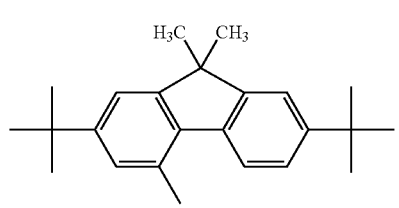 [SMILES: Cc1cc(C(C)(C)C)cc2c1-c1ccc(C(C)(C)C)cc1C2(C)C]

-continued
55 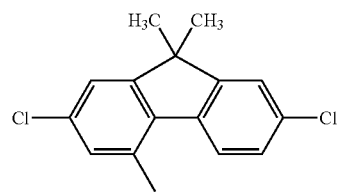 [SMILES: Cc1cc(Cl)cc2c1-c1ccc(Cl)cc1C2(C)C]
56 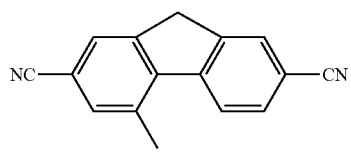
57 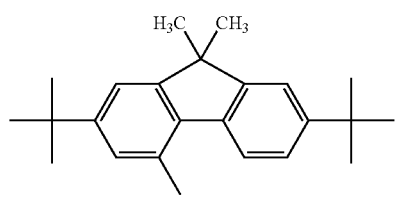 [SMILES: Cc1cc(C(C)(C)C)cc2c1-c1ccc(C(C)(C)C)cc1C2(C)C]
58 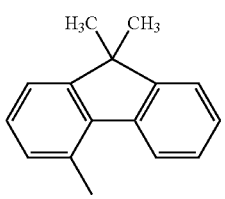 [SMILES: Cc1cccc2c1-c1ccccc1C2(C)C]
59 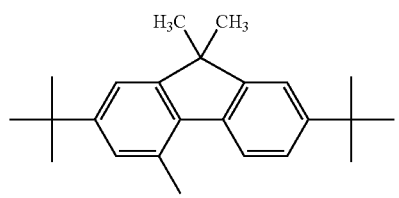 [SMILES: Cc1cc(C(C)(C)C)cc2c1-c1ccc(C(C)(C)C)cc1C2(C)C]
60 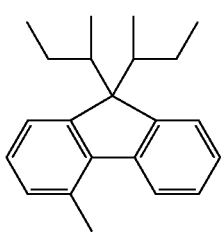 [SMILES: CCC(C)C1(C(C)CC)c2ccccc2-c2c(C)cccc21]
61 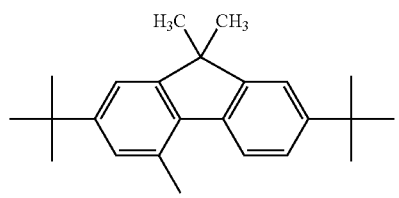
62 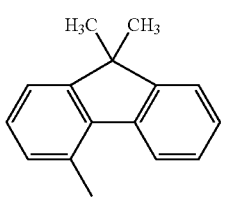 [SMILES: Cc1cccc2c1-c1ccccc1C2(C)C]

-continued
63 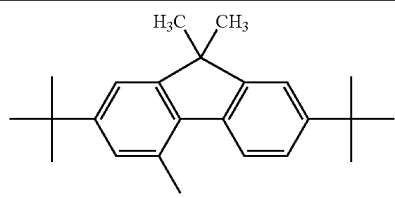
64 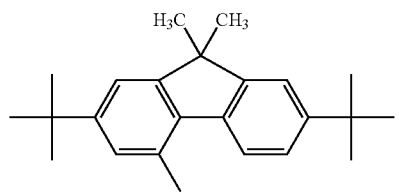 [SMILES: Cc1cc(C(C)(C)C)cc2c1-c1ccc(C(C)(C)C)cc1C2(C)C]
65 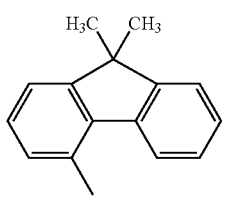 [SMILES: Cc1cccc2c1-c1ccccc1C2(C)C]
66 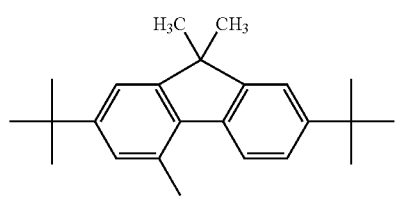 [SMILES: Cc1cc(C(C)(C)C)cc2c1-c1ccc(C(C)(C)C)cc1C2(C)C]
67 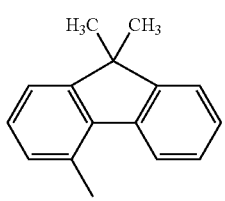 [SMILES: Cc1cccc2c1-c1ccccc1C2(C)C]
68 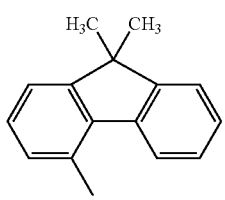 [SMILES: Cc1cccc2c1-c1ccccc1C2(C)C]
69 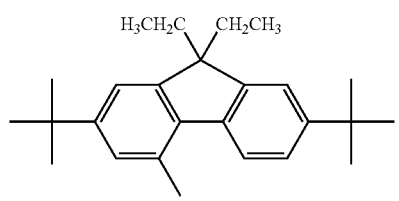
| Compound No. | Ar 1 |
|---|---|
| 1 | 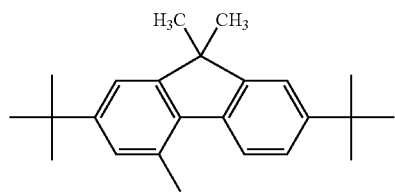 [SMILES: Cc1cc(C(C)(C)C)cc2c1-c1ccc(C(C)(C)C)cc1C2(C)C] |

-continued
2 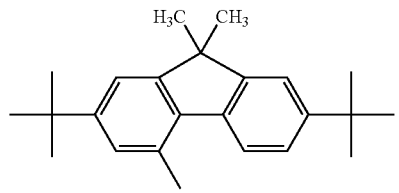 [SMILES: Cc1cc(C(C)(C)C)cc2c1-c1ccc(C(C)(C)C)cc1C2(C)C]
3 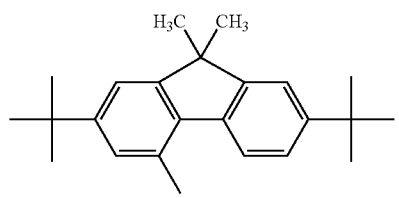 [SMILES: Cc1cc(C(C)(C)C)cc2c1-c1ccc(C(C)(C)C)cc1C2(C)C]
4 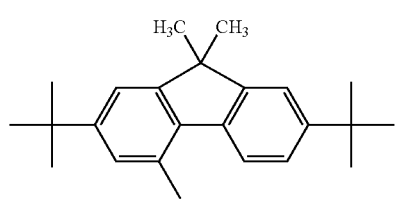
5 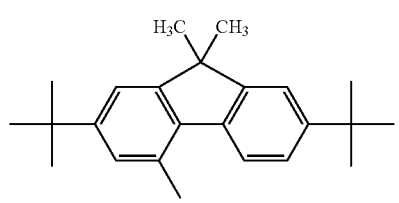 [SMILES: Cc1cc(C(C)(C)C)cc2c1-c1ccc(C(C)(C)C)cc1C2(C)C]
6 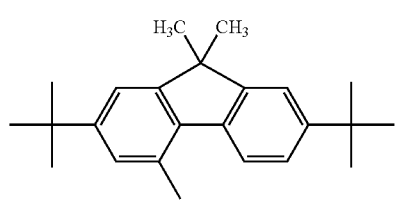
7 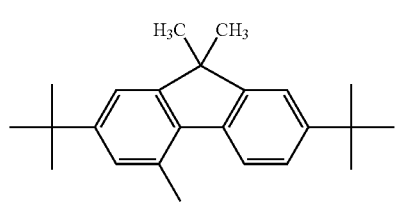 [SMILES: Cc1cc(C(C)(C)C)cc2c1-c1ccc(C(C)(C)C)cc1C2(C)C]
8 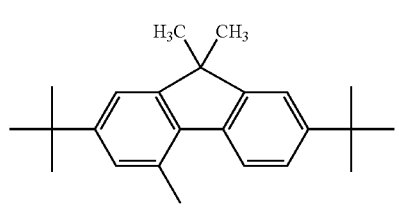 [SMILES: Cc1cc(C(C)(C)C)cc2c1-c1ccc(C(C)(C)C)cc1C2(C)C]
9 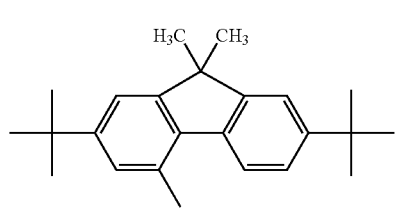 [SMILES: Cc1cc(C(C)(C)C)cc2c1-c1ccc(C(C)(C)C)cc1C2(C)C]

-continued
10
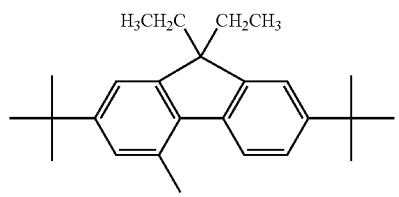
11
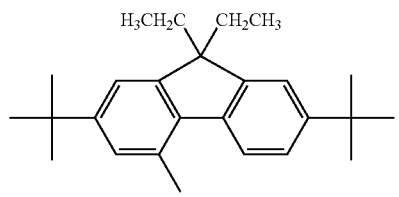
12
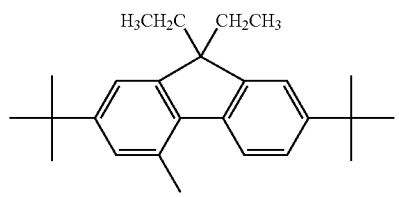
13
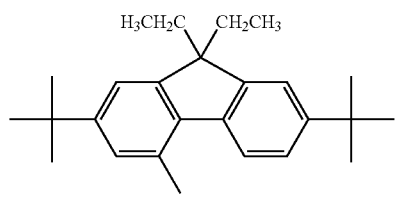
14
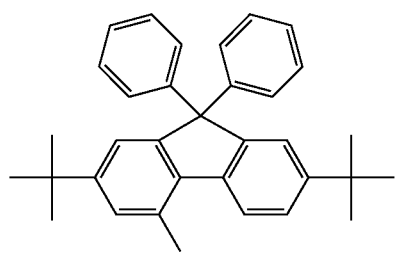 [SMILES: Cc1cc(C(C)(C)C)cc2c1-c1ccc(C(C)(C)C)cc1C2(c1ccccc1)c1ccccc1]
15
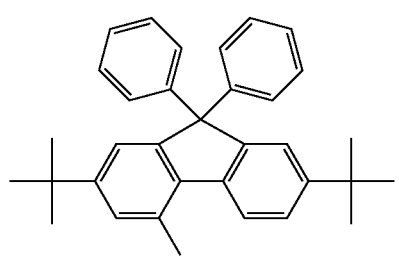 [SMILES: Cc1cc(C(C)(C)C)cc2c1-c1ccc(C(C)(C)C)cc1C2(c1ccccc1)c1ccccc1]
16
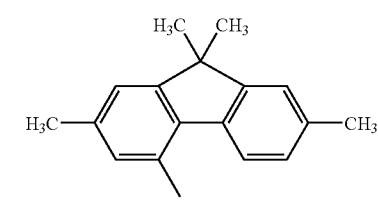

-continued
17
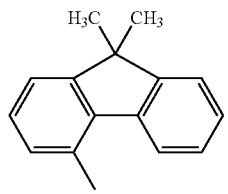 [SMILES: Cc1cccc2c1-c1ccccc1C2(C)C]
18
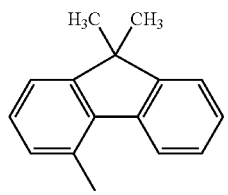 [SMILES: Cc1cccc2c1-c1ccccc1C2(C)C]
19
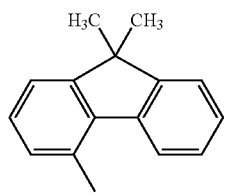 [SMILES: Cc1cccc2c1-c1ccccc1C2(C)C]
20
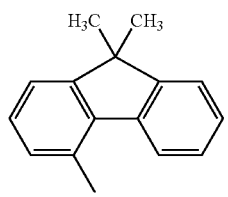 [SMILES: Cc1cccc2c1-c1ccccc1C2(C)C]
21
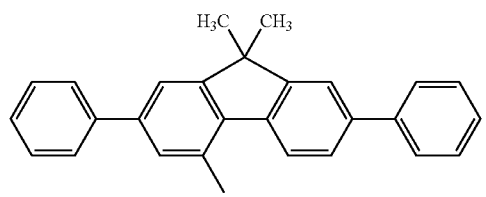 [SMILES: Cc1cc(-c2ccccc2)cc2c1-c1ccc(-c3ccccc3)cc1C2(C)C]
22
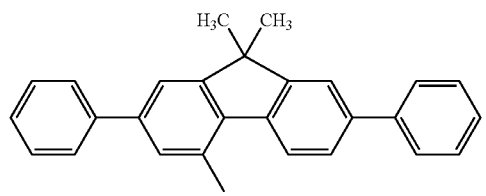
23
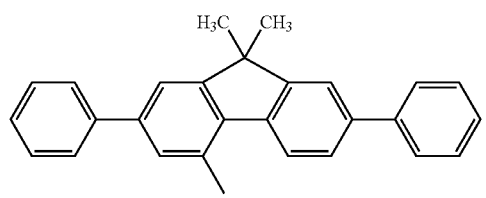 [SMILES: Cc1cc(-c2ccccc2)cc2c1-c1ccc(-c3ccccc3)cc1C2(C)C]

-continued
24
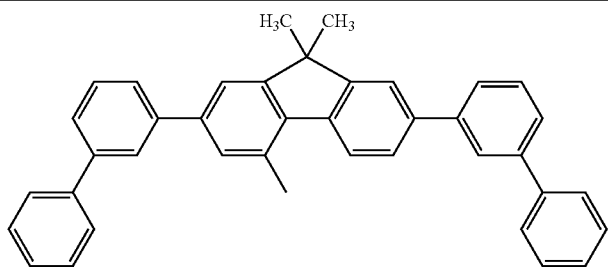
25
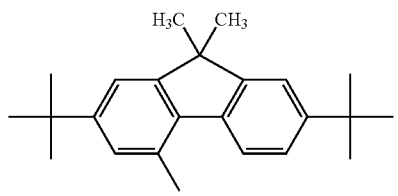 [SMILES: Cc1cc(C(C)(C)C)cc2c1-c1ccc(C(C)(C)C)cc1C2(C)C]
26
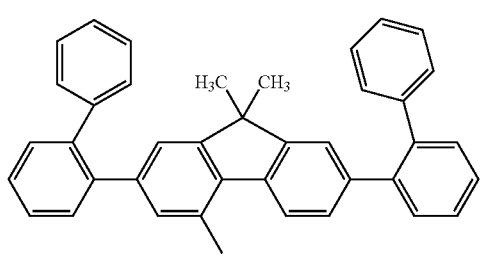 [SMILES: Cc1cc(-c2ccccc2-c2ccccc2)cc2c1-c1ccc(-c3ccccc3-c3ccccc3)cc1C2(C)C]
27
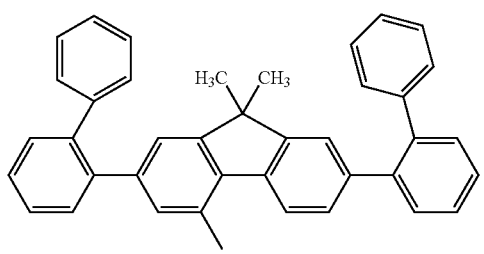 [SMILES: Cc1cc(-c2ccccc2-c2ccccc2)cc2c1-c1ccc(-c3ccccc3-c3ccccc3)cc1C2(C)C]
28
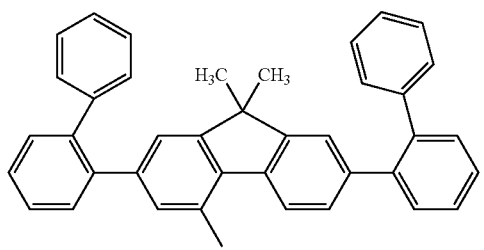 [SMILES: Cc1cc(-c2ccccc2-c2ccccc2)cc2c1-c1ccc(-c3ccccc3-c3ccccc3)cc1C2(C)C]
29
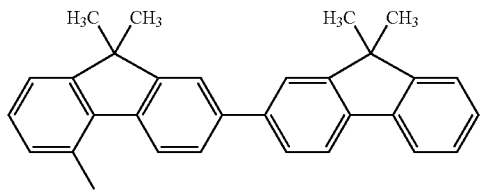 [SMILES: Cc1cccc2c1-c1ccc(-c3ccc4c(c3)C(C)(C)c3ccccc3-4)cc1C2(C)C]
30
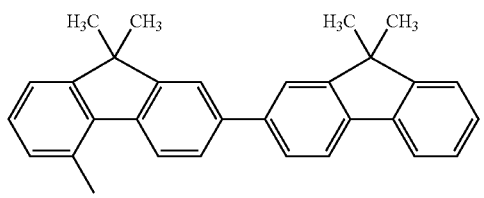 [SMILES: Cc1cccc2c1-c1ccc(-c3ccc4c(c3)C(C)(C)c3ccccc3-4)cc1C2(C)C]

| | |
|---|---|
| 31 | 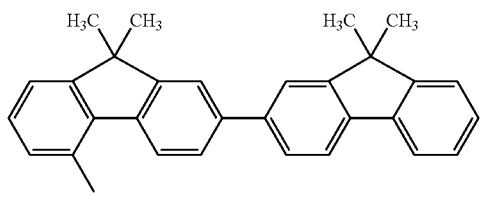 [SMILES: Cc1cccc2c1-c1ccc(-c3ccc4c(c3)C(C)(C)c3ccccc3-4)cc1C2(C)C] |
| 32 | 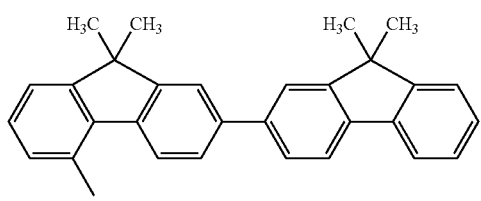 |
| 33 | 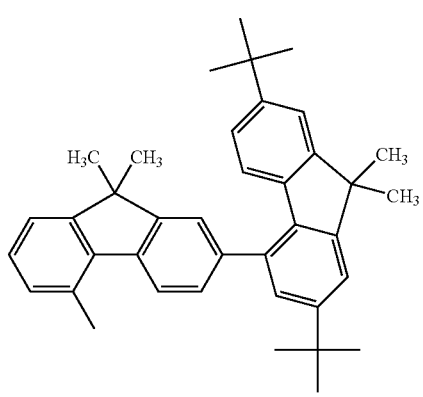 [SMILES: Cc1cccc2c1-c1ccc(-c3cc(C(C)(C)C)cc4c3-c3ccc(C(C)(C)C)cc3C4(C)C)cc1C2(C)C] |
| 34 | 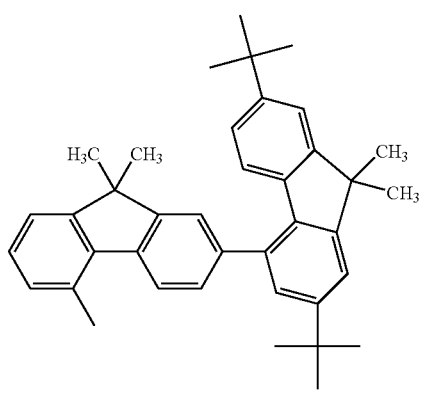 [SMILES: Cc1cccc2c1-c1ccc(-c3cc(C(C)(C)C)cc4c3-c3ccc(C(C)(C)C)cc3C4(C)C)cc1C2(C)C] |
| 35 | 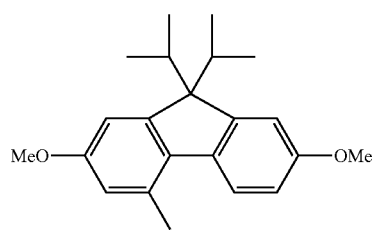 [SMILES: COc1ccc2c(c1)C(C(C)C)(C(C)C)c1cc(OC)cc(C)c1-2] |
| 36 | 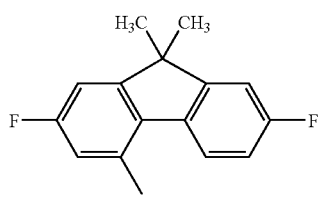 [SMILES: Cc1cc(F)cc2c1-c1ccc(F)cc1C2(C)C] |

| | |
|---|---|
| 37 | 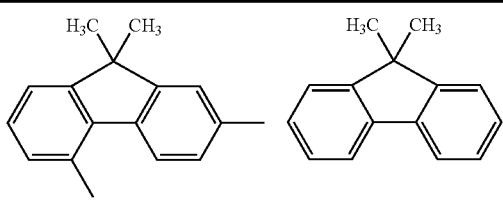 |
| 38 | 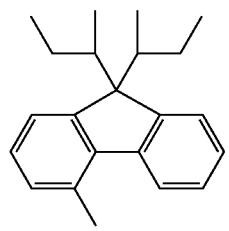 [SMILES: CCC(C)C1(C(C)CC)c2ccccc2-c2c(C)cccc21] |
| 39 | 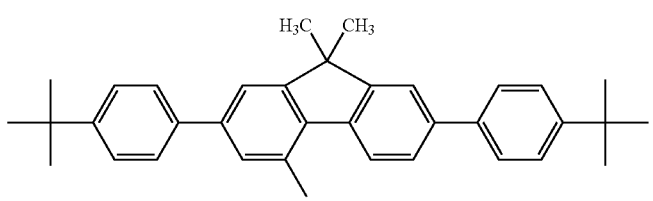 [SMILES: Cc1cc(-c2ccc(C(C)(C)C)cc2)cc2c1-c1ccc(-c3ccc(C(C)(C)C)cc3)cc1C2(C)C] |
| 40 | 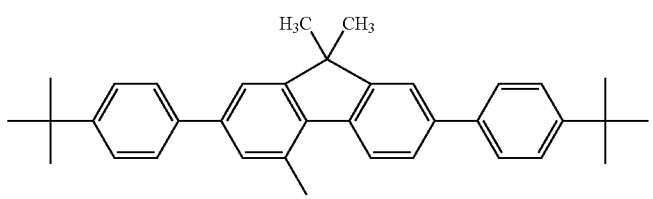 [SMILES: Cc1cc(-c2ccc(C(C)(C)C)cc2)cc2c1-c1ccc(-c3ccc(C(C)(C)C)cc3)cc1C2(C)C] |
| 41 | 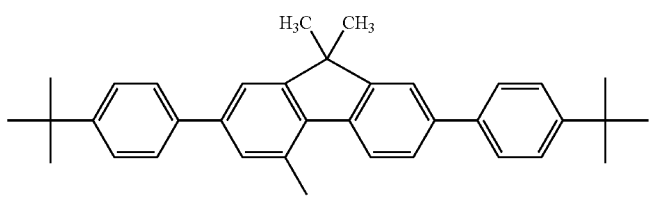 |
| 42 | 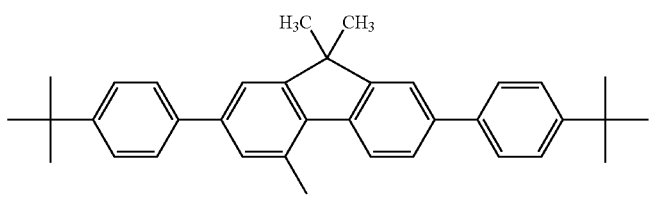 [SMILES: Cc1cc(-c2ccc(C(C)(C)C)cc2)cc2c1-c1ccc(-c3ccc(C(C)(C)C)cc3)cc1C2(C)C] |
| 43 | 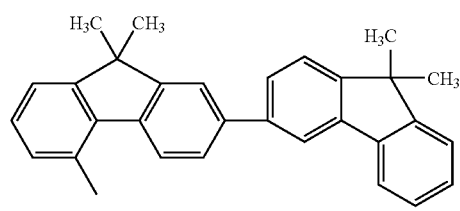 [SMILES: Cc1cccc2c1-c1ccc(-c3ccc4c(c3)-c3ccccc3C4(C)C)cc1C2(C)C] |
| 44 | 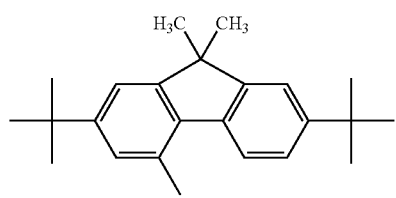 |

-continued
| | |
|---|---|
| 45 | 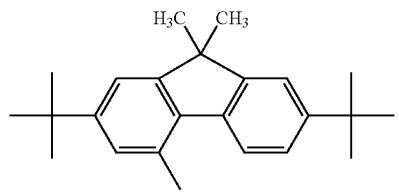 [SMILES: Cc1cc(C(C)(C)C)cc2c1-c1ccc(C(C)(C)C)cc1C2(C)C] |
| 46 | 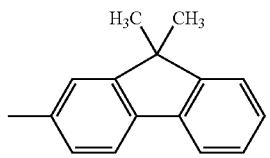 [SMILES: Cc1ccc2c(c1)C(C)(C)c1ccccc1-2] |
| 47 | 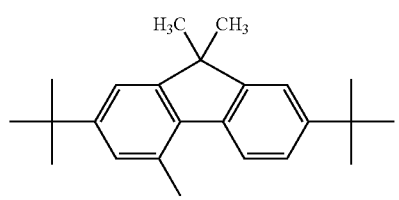 |
| 48 | 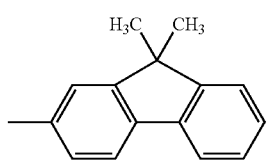 [SMILES: Cc1ccc2c(c1)C(C)(C)c1ccccc1-2] |
| 49 | 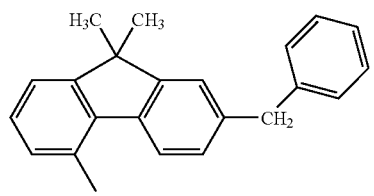 [SMILES: Cc1cccc2c1-c1ccc(Cc3ccccc3)cc1C2(C)C] |
| 50 | 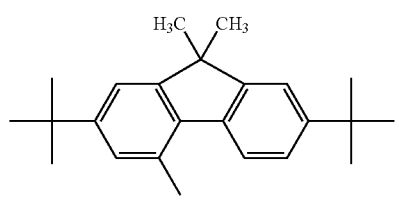 [SMILES: Cc1cc(C(C)(C)C)cc2c1-c1ccc(C(C)(C)C)cc1C2(C)C] |
| 51 | 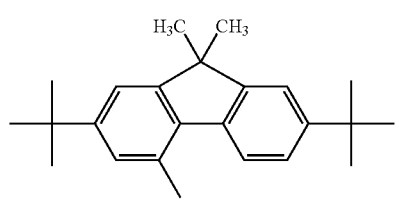 |
| 52 | 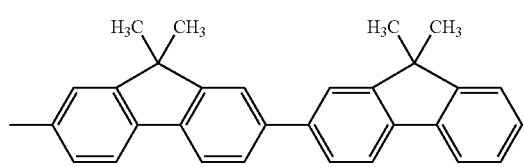 [SMILES: Cc1ccc2c(c1)C(C)(C)c1cc(-c3ccc4c(c3)C(C)(C)c3ccccc3-4)ccc1-2] |

-continued
| | |
|---|---|
| 53 | 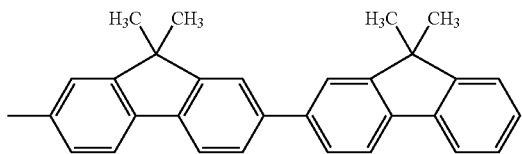 [SMILES: Cc1ccc2c(c1)C(C)(C)c1cc(-c3ccc4c(c3)C(C)(C)c3ccccc3-4)ccc1-2] |
| 54 | 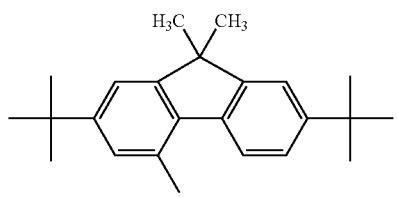 [SMILES: Cc1cc(C(C)(C)C)cc2c1-c1ccc(C(C)(C)C)cc1C2(C)C] |
| 55 | 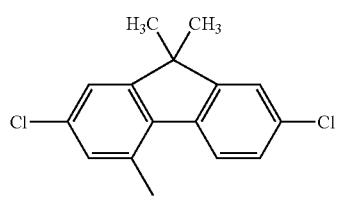 [SMILES: Cc1cc(Cl)cc2c1-c1ccc(Cl)cc1C2(C)C] |
| 56 | 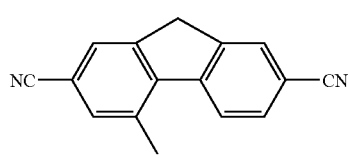 |
| 57 | 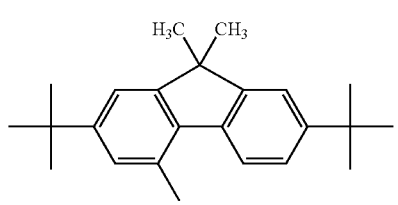 [SMILES: Cc1cc(C(C)(C)C)cc2c1-c1ccc(C(C)(C)C)cc1C2(C)C] |
| 58 | 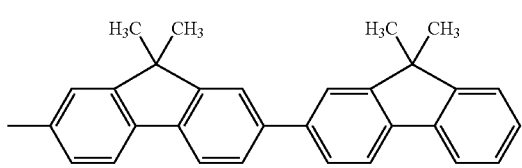 [SMILES: Cc1ccc2c(c1)C(C)(C)c1cc(-c3ccc4c(c3)C(C)(C)c3ccccc3-4)ccc1-2] |
| 59 | 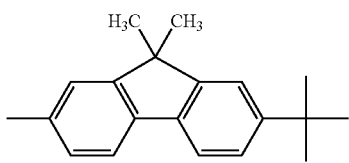 |
| 60 | 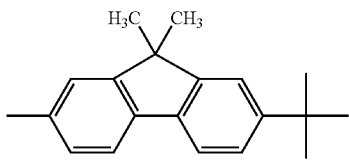 |
| 61 | 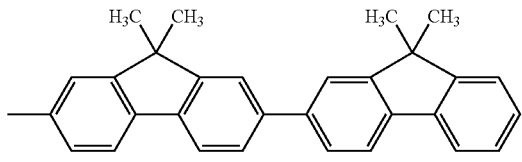 [SMILES: Cc1ccc2c(c1)C(C)(C)c1cc(-c3ccc4c(c3)C(C)(C)c3ccccc3-4)ccc1-2] |

| | |
|---|---|
| 62 | 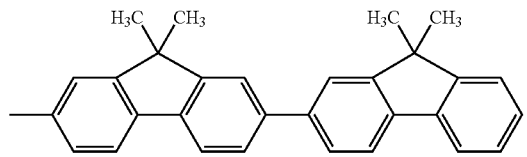 [SMILES: Cc1ccc2c(c1)C(C)(C)c1cc(-c3ccc4c(c3)C(C)(C)c3ccccc3-4)ccc1-2] |
| 63 | 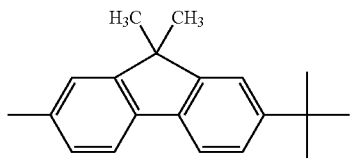 [SMILES: Cc1ccc2c(c1)C(C)(C)c1cc(C(C)(C)C)ccc1-2] |
| 64 | 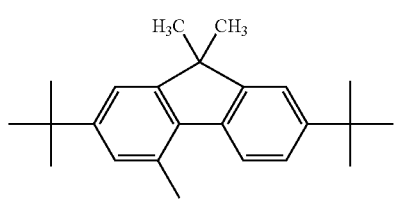 [SMILES: Cc1cc(C(C)(C)C)cc2c1-c1ccc(C(C)(C)C)cc1C2(C)C] |
| 65 | 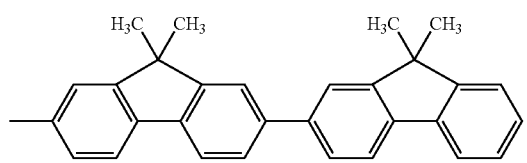 [SMILES: Cc1ccc2c(c1)C(C)(C)c1cc(-c3ccc4c(c3)C(C)(C)c3ccccc3-4)ccc1-2] |
| 66 | 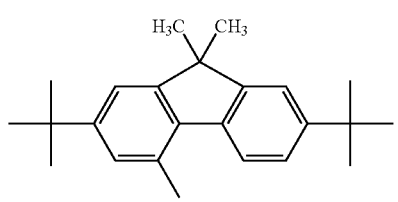 |
| 67 | 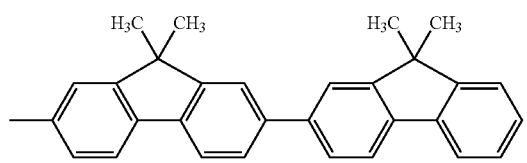 [SMILES: Cc1ccc2c(c1)C(C)(C)c1cc(-c3ccc4c(c3)C(C)(C)c3ccccc3-4)ccc1-2] |
| 68 | 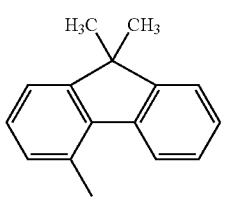 [SMILES: Cc1cccc2c1-c1ccccc1C2(C)C] |
| 69 | 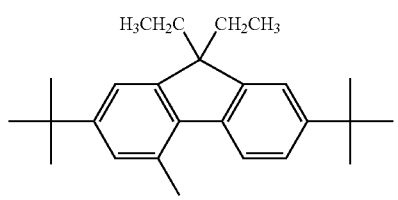 |

-continued
| Compound No. | Ar 2 |
|---|---|
| 1 | 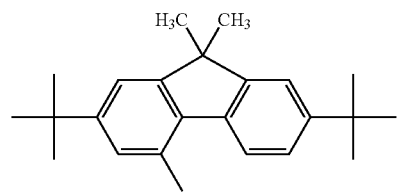 [SMILES: Cc1cc(C(C)(C)C)cc2c1-c1ccc(C(C)(C)C)cc1C2(C)C] |
| 2 | 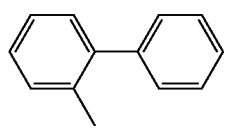 |
| 3 | 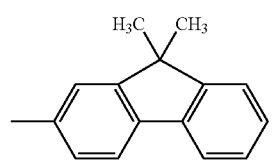 [SMILES: Cc1ccc2c(c1)C(C)(C)c1ccccc1-2] |
| 4 | 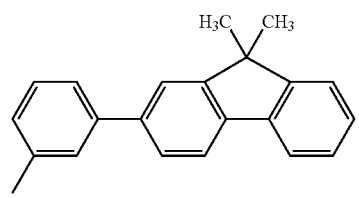 [SMILES: Cc1cccc(-c2ccc3c(c2)C(C)(C)c2ccccc2-3)c1] |
| 5 | 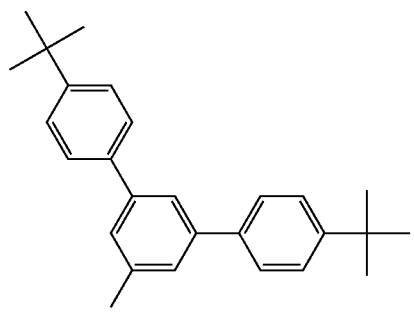 [SMILES: Cc1cc(-c2ccc(C(C)(C)C)cc2)cc(-c2ccc(C(C)(C)C)cc2)c1] |
| 6 | 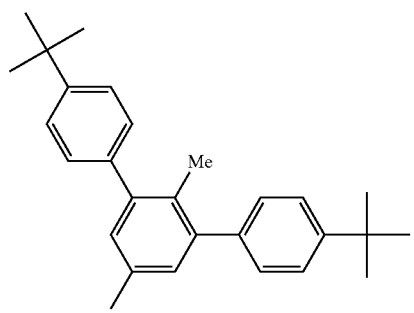 [SMILES: Cc1cc(-c2ccc(C(C)(C)C)cc2)c(C)c(-c2ccc(C(C)(C)C)cc2)c1] |
| 7 | 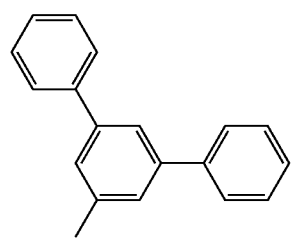 [SMILES: Cc1cc(-c2ccccc2)cc(-c2ccccc2)c1] |

-continued
| | |
|---|---|
| 8 | 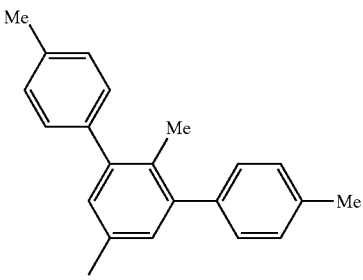 [SMILES: Cc1ccc(-c2cc(C)cc(-c3ccc(C)cc3)c2C)cc1] |
| 9 | 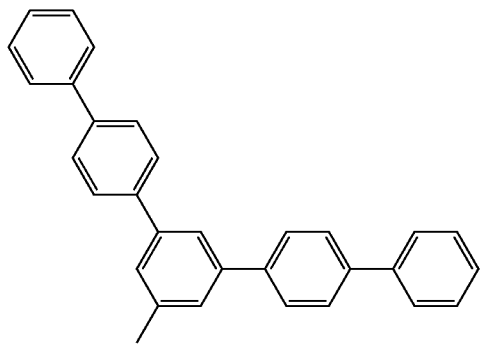 [SMILES: Cc1cc(-c2ccc(-c3ccccc3)cc2)cc(-c2ccc(-c3ccccc3)cc2)c1] |
| 10 | 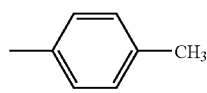 |
| 11 | 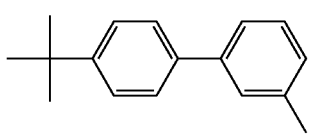 [SMILES: Cc1cccc(-c2ccc(C(C)(C)C)cc2)c1] |
| 12 | 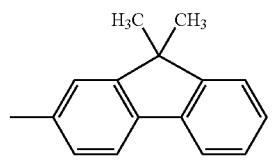 [SMILES: Cc1ccc2c(c1)C(C)(C)c1ccccc1-2] |
| 13 | 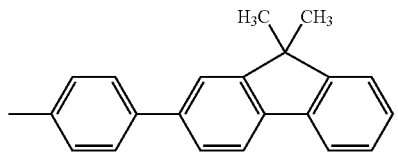 |
| 14 | 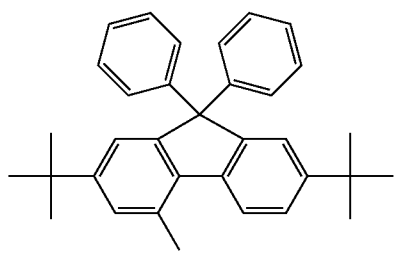 [SMILES: Cc1cc(C(C)(C)C)cc2c1-c1ccc(C(C)(C)C)cc1C2(c1ccccc1)c1ccccc1] |
| 15 | 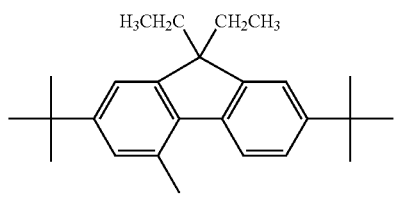 |

-continued
16 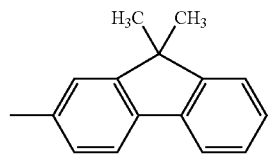 [SMILES: Cc1ccc2c(c1)C(C)(C)c1ccccc1-2]
17 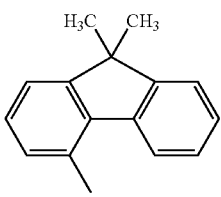 [SMILES: Cc1cccc2c1-c1ccccc1C2(C)C]
18 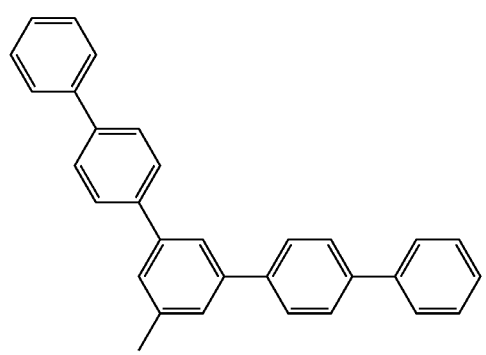 [SMILES: Cc1cc(-c2ccc(-c3ccccc3)cc2)cc(-c2ccc(-c3ccccc3)cc2)c1]
19 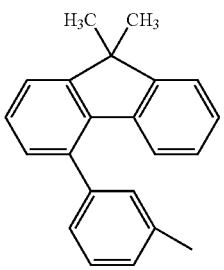 [SMILES: Cc1cccc(-c2cccc3c2-c2ccccc2C3(C)C)c1]
20 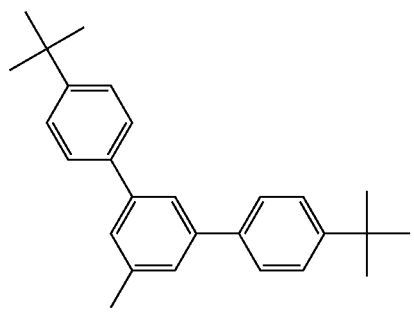 [SMILES: Cc1cc(-c2ccc(C(C)(C)C)cc2)cc(-c2ccc(C(C)(C)C)cc2)c1]
21 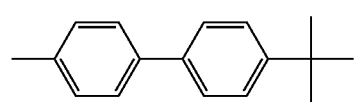
22 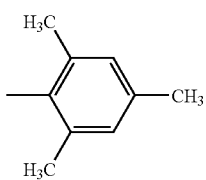

-continued
23 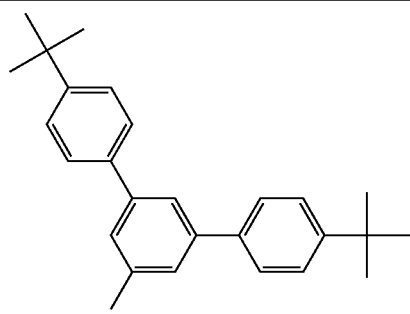
24 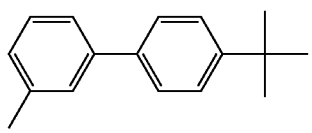 [SMILES: Cc1cccc(-c2ccc(C(C)(C)C)cc2)c1]
25 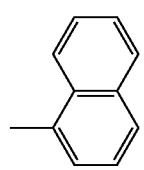
26 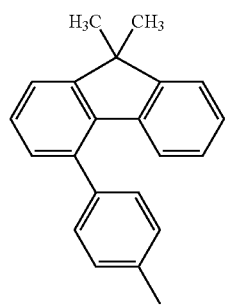 [SMILES: Cc1ccc(-c2cccc3c2-c2ccccc2C3(C)C)cc1]
27 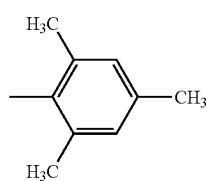
28 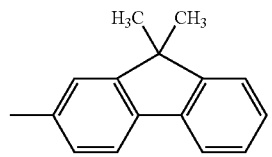 [SMILES: Cc1ccc2c(c1)C(C)(C)c1ccccc1-2]
29 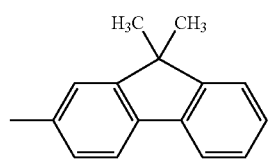 [SMILES: Cc1ccc2c(c1)C(C)(C)c1ccccc1-2]
30 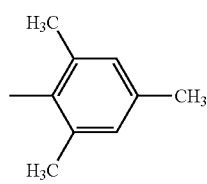

-continued
| | |
|---|---|
| 31 | 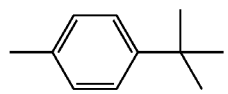 |
| 32 | 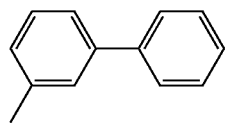 |
| 33 | 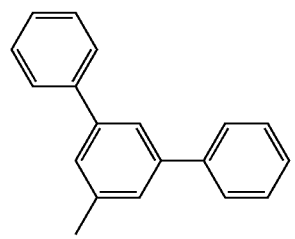 [SMILES: Cc1cc(-c2ccccc2)cc(-c2ccccc2)c1] |
| 34 | 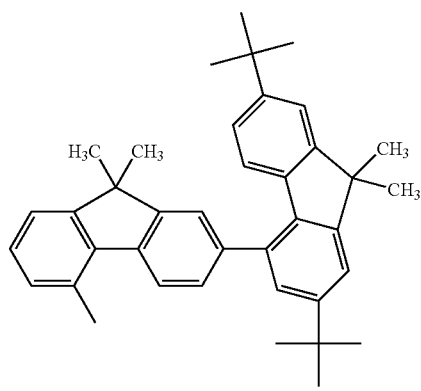 [SMILES: Cc1cccc2c1-c1ccc(-c3cc(C(C)(C)C)cc4c3-c3ccc(C(C)(C)C)cc3C4(C)C)cc1C2(C)C] |
| 35 |  |
| 36 | 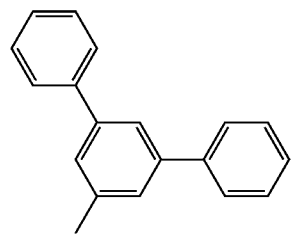 |
| 37 | 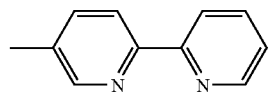 |
| 38 | 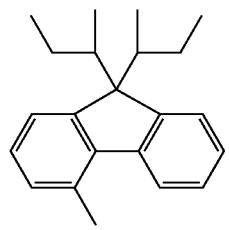 [SMILES: CCC(C)C1(C(C)CC)c2ccccc2-c2c(C)cccc21] |

-continued
39 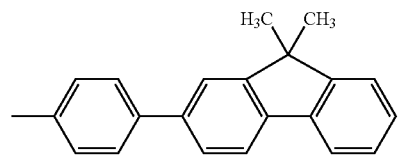 [SMILES: Cc1ccc(-c2ccc3c(c2)C(C)(C)c2ccccc2-3)cc1]
40 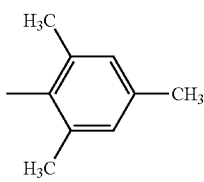
41 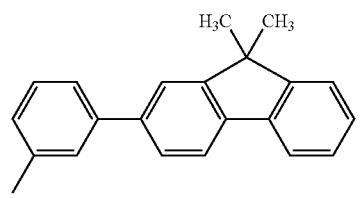 [SMILES: Cc1cccc(-c2ccc3c(c2)C(C)(C)c2ccccc2-3)c1]
42 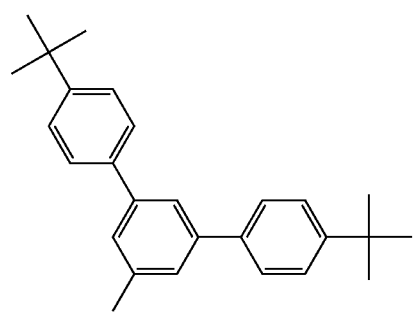 [SMILES: Cc1cc(-c2ccc(C(C)(C)C)cc2)cc(-c2ccc(C(C)(C)C)cc2)c1]
43 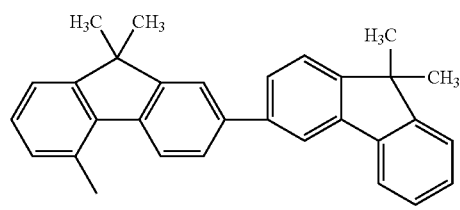 [SMILES: Cc1cccc2c1-c1ccc(-c3ccc4c(c3)-c3ccccc3C4(C)C)cc1C2(C)C]
44 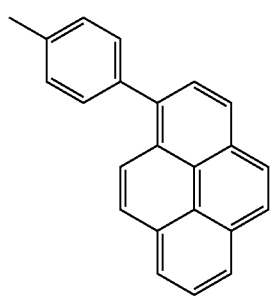 [SMILES: Cc1ccc(-c2ccc3ccc4cccc5ccc2c3c45)cc1]
45 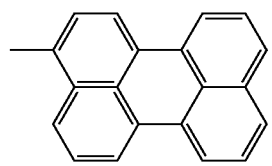

-continued
| | |
|---|---|
| 46 | 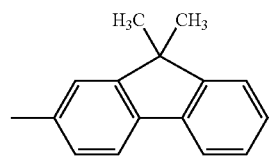 [SMILES: Cc1ccc2c(c1)C(C)(C)c1ccccc1-2] |
| 47 | 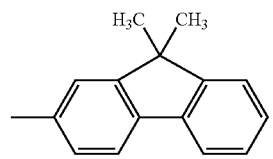 [SMILES: Cc1ccc2c(c1)C(C)(C)c1ccccc1-2] |
| 48 | 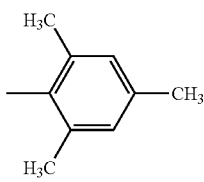 |
| 49 | 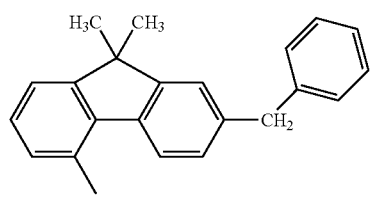 [SMILES: Cc1cccc2c1-c1ccc(Cc3ccccc3)cc1C2(C)C] |
| 50 | 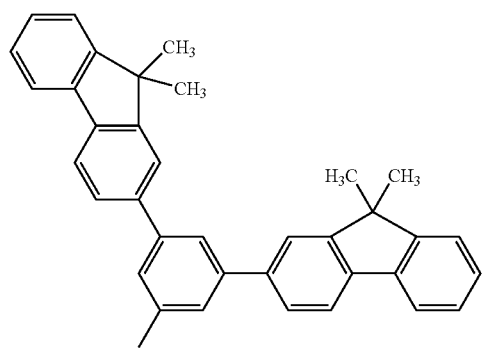 [SMILES: Cc1cc(-c2ccc3c(c2)C(C)(C)c2ccccc2-3)cc(-c2ccc3c(c2)C(C)(C)c2ccccc2-3)c1] |
| 51 | 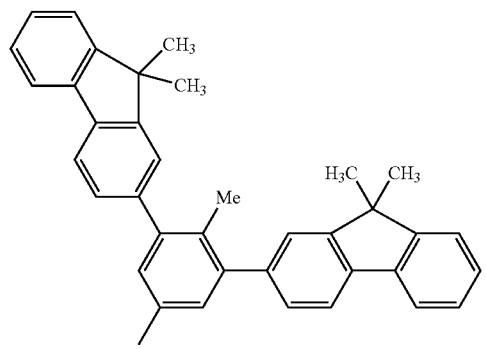 [SMILES: Cc1cc(-c2ccc3c(c2)C(C)(C)c2ccccc2-3)c(C)c(-c2ccc3c(c2)C(C)(C)c2ccccc2-3)c1] |
| 52 | 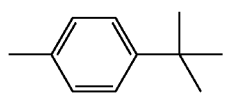 |

-continued
53 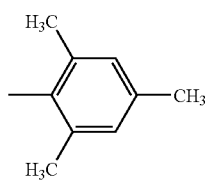
54 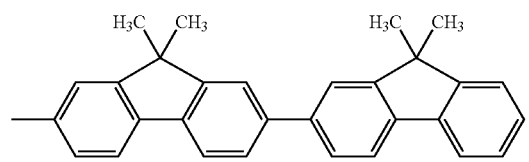
55 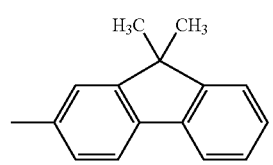
56 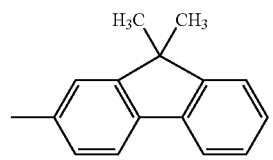 [SMILES: Cc1ccc2c(c1)C(C)(C)c1ccccc1-2]
57 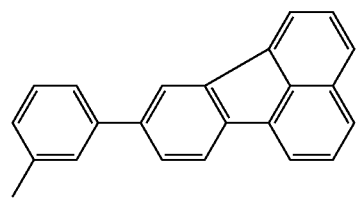 [SMILES: Cc1cccc(-c2ccc3c(c2)-c2cccc4cccc-3c24)c1]
58 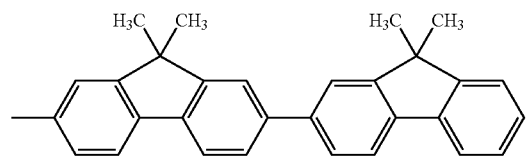 [SMILES: Cc1ccc2c(c1)C(C)(C)c1cc(-c3ccc4c(c3)C(C)(C)c3ccccc3-4)ccc1-2]
59 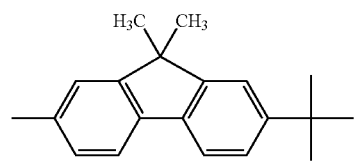 [SMILES: Cc1ccc2c(c1)C(C)(C)c1cc(C(C)(C)C)ccc1-2]
60 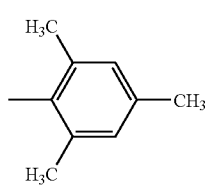
61 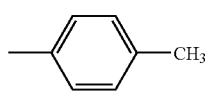
62 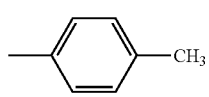

63 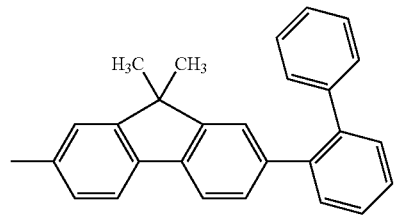 [SMILES: Cc1ccc2c(c1)C(C)(C)c1cc(-c3ccccc3-c3ccccc3)ccc1-2]
64 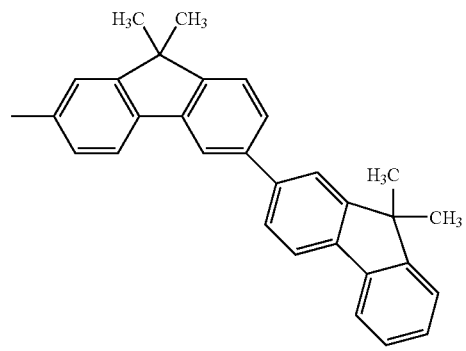 [SMILES: Cc1ccc2c(c1)C(C)(C)c1ccc(-c3ccc4c(c3)C(C)(C)c3ccccc3-4)cc1-2]
65 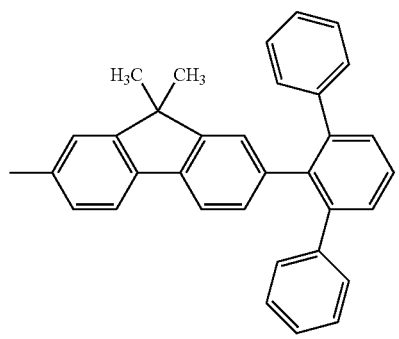 [SMILES: Cc1ccc2c(c1)C(C)(C)c1cc(-c3c(-c4ccccc4)cccc3-c3ccccc3)ccc1-2]
66 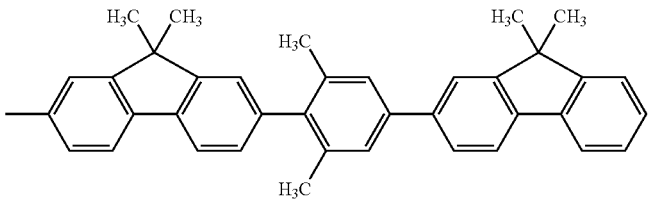 [SMILES: Cc1ccc2c(c1)C(C)(C)c1cc(-c3c(C)cc(-c4ccc5c(c4)C(C)(C)c4ccccc4-5)cc3C)ccc1-2]
67 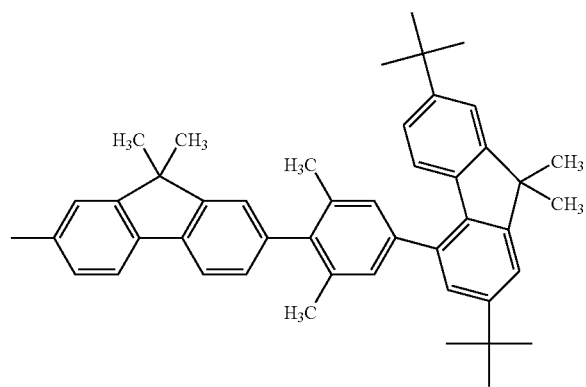

| | |
|---|---|
| 68 | 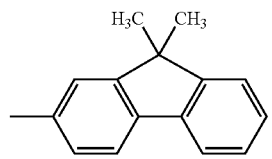 |
| 69 | 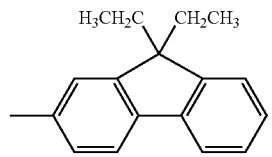 |

Next, an organic light emitting device of the present invention will be described in detail.

An organic light emitting device of the present invention includes: a pair of electrodes composed of an anode and a cathode; and a layer containing an organic compound and being interposed between the pair of electrodes, in which the layer containing the organic compound contains at least one kind of compounds represented by the general formula (1).

In addition, in the present invention, in an organic light emitting device including: a pair of electrodes composed of an anode and a cathode; and plural layers each containing an organic compound, the plural layers being interposed between the pair of electrodes, a second hole transport layer is laminated to be adjacent to an organic light emitting layer on the anode side of the light emitting layer, and, furthermore, a first hole transport layer is laminated as another layer to be adjacent to the second hole transport layer. Here, each of the first and second hole transport layers is a layer excellent in ability to transport a hole from the anode to the light emitting layer.

In general, two hole transport layers are laminated, a material having an ionization potential close to that of an anode is used in a first hole transport layer adjacent to a i anode interface, and a material having a wide band gap is used in a second hole transport layer adjacent to a ii light emitting layer. The above layers i and ii exert effects on the following items i' and ii', respectively, and can derive the following device characteristics i" and ii", respectively.

i': improvement in property with which a hole is injected from the anode into an organic layer ii': entrapment of a carrier and an exciton in the light emitting layer i": reduction in voltage at which the device is driven ii": improvement in external quantum efficiency In the present invention, the second hole transport layer contains at least one kind of a compound containing one tertiary amine skeleton. First, the presence of a tertiary amine skeleton can improve a hole mobility. Further, setting the number of tertiary amine skeletons to 1 shortens a conjugation length. The shortening is useful in molecular design for widening a band gap. Here, the 4-aminofluorene compound represented by the above general formula (1) of the present invention constitutes a non-planar molecular shape, so a material having an additionally wide band gap can be easily obtained. Accordingly, a carrier and an exciton of the light emitting layer can be effectively trapped in the light emitting layer. The entrapment is effective for an improvement in external quantum efficiency of the organic light emitting device and for a reduction in voltage at which the device is driven. Here, the second hole transport layer may be constituted only of a compound containing one amine skeleton, or may contain any other compound.

In addition, the first hole transport layer contains at least one kind of a compound containing one tertiary amine skeleton. Setting the number of tertiary amine skeletons to 1 facilitates the design of a molecule having a low molecular weight as compared to a compound having 2 or more tertiary amine skeletons. The facilitation is useful in providing a material having good deposition property or a material having a wide band gap. The application of a compound having a wide band gap neither inhibits (reabsorbs) the light emission of even a dopant (guest) which is present in the light emitting layer and which emits light having a short wavelength nor causes a reduction in efficiency with which the dopant emits light. In addition, the first hole transport layer may be constituted only of a compound containing one non-cyclic tertiary amine skeleton, or may contain any other compound.

In addition, each of the first hole transport layer and the second hole transport layer preferably contains a compound containing at least one non-cyclic tertiary amine skeleton. The term "non-cyclic tertiary amine" as used herein refers to a tertiary amine whose substituents are not bonded to each other, and do not form a ring. The substituents of the tertiary amine are not bonded to each other, so the degree of freedom in the rotation of a molecular structure increases. The increase is useful in the design of a molecule having a short conjugation length. The widening of the band gap of the first hole transport layer can prevent reabsorption as in the case of the foregoing. In addition, the widening of the band gap of the second hole transport layer enables a carrier and an exciton to be effectively trapped in the light emitting layer.

In addition, the 4-aminofluorene compound represented by the above general formula (1) of the present invention is preferably incorporated as a compound of which each of the first hole transport layer and the second hole transport layer is formed. The 4-aminofluorene compound has higher steric hindrance and a shorter conjugation length than those of any other compound because 4-position of a tertiary amine is substituted by a fluorene group. Accordingly, a hole transport material having an additionally wide band gap and a high glass transition temperature can be obtained. Further, the application of a material having a high glass transition temperature to each of the first hole transport layer and the second hole transport layer can improve the durability of the device. In addition, the band gap of a tertiary amine compound having one nitrogen atom and present in the second hole transport layer is preferably wider than that of a compound the content of which in the light emitting layer is highest. Here, the content of the compound the content of which is highest is represented by wt %. To be specific, when the light emitting layer contains a host and a guest, the compound the content of which is highest often serves as the host. Satisfying the order of the band gaps can improve the property with which a hole is injected into the light emitting layer, and can effectively reduce the leak of an electron to the second hole transport layer. A band gap can be measured from an ultraviolet-visible light absorption spectrum. In the present invention, a band gap was determined from an absorption end of a thin film formed on a glass substrate by using a spectrophotometer U-3010 manufactured by Hitachi, Ltd. as a measuring apparatus.

In addition, a preferable device constitution is such that an ionization potential Ip1 of a compound the content of which in the first hole transport layer is highest, an ionization potential Ip2 of a compound the content of which in the second hole transport layer is highest, and an ionization potential Ip3 of the compound the content of which in the light emitting layer is highest satisfy the relationship of Ip1<Ip2<Ip3.

When Ip2 is intermediate between Ip1 and Ip3, the property with which a hole is injected from the anode into the light emitting layer can be improved without the occurrence of extremely large injection barriers at some interfaces. In view of the foregoing, the voltage at which the device is driven can be effectively reduced by forming a device constitution in which the ionization potentials satisfy the above relationship. Here, an ionization potential was measured by employing a photoelectron spectroscopy approach in the air (measuring instrument name AC-1 manufactured by RIKENKIKI CO., LTD).

FIGS. 1, 2, 3 and 4 each show a preferable example of the organic light emitting device of the present invention.

FIG. 1 is a sectional view showing an example of the organic light emitting device of the present invention. FIG. 1 shows a constitution in which the anode 2, the light emitting layer 3, and the cathode 4 are sequentially provided onto the substrate 1. The light emitting device to be used here is useful in a case where the device itself has properties such as a hole-transporting ability, an electron-transporting ability, and light emitting properties alone or a case where compounds having respective properties are used as a mixture.

Figure 2:
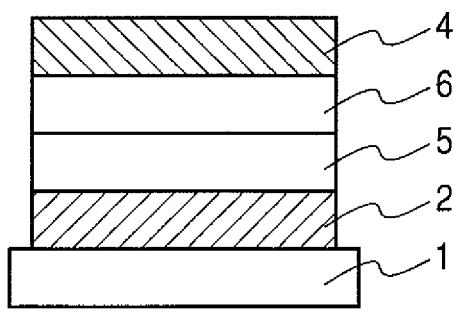
FIG. 2 is a sectional view showing another example of the organic light emitting device in the present invention.

FIG. 2 is a sectional view showing another example of the organic light emitting device of the present invention. FIG. 2 shows a constitution in which the anode 2, the hole transport layer 5, the electron transport layer 6, and the cathode 4 are sequentially provided onto the substrate 1. In this case, a material having one or both of hole-transporting property and electron-transporting property is used as a light-emitting substance in each layer. This case is useful when the device is used in combination with a mere hole-transporting substance or electron-transporting substance having no light emitting properties. In addition, in this case, a light emitting layer 3 is composed of one of the hole transport layer 5 and the electron transport layer 6.

Figure 3:
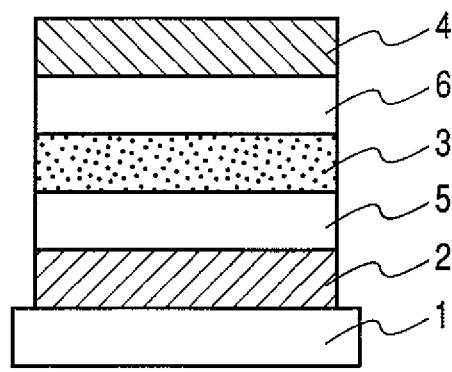
FIG. 3 is a sectional view showing another example of the organic light emitting device in the present invention.

FIG. 3 is a sectional view showing another example of the organic light emitting device of the present invention. FIG. 3 shows a constitution in which the anode 2, the hole transport layer 5, the light emitting layer 3, the electron transport layer 6, and the cathode 4 are sequentially provided onto the substrate 1. This constitution separates a carrier-transporting function and a light-emitting function. In addition, the device can be timely used in combination with a compound having respective properties such as a hole-transporting property, an electron-transporting property, and light emitting properties, so the degree of freedom in selection of a material extremely increases. In addition, various compounds different from each other in emission wavelength can be used. As a result, the range of luminescent colors can be widened. Furthermore, a luminous efficiency can be improved by effectively trapping each carrier or exciton in the central light emitting layer 3.

Figure 4:
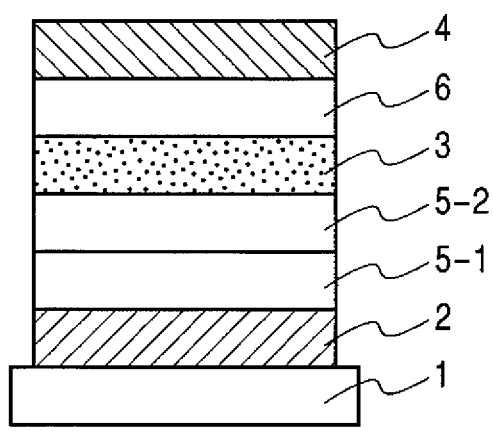
FIG. 4 is a sectional view showing another example of the organic light emitting device in the present invention.

FIG. 4 is a sectional view showing another example in the organic light emitting device of the present invention. FIG. 4 shows a structure different from that shown in FIG. 3 in that two layers, that is, the first hole transport layer 5-1 and the second hole transport layer 5-2 are laminated instead of a single hole transport layer. The structure is excellent in hole injection property and property with which a hole is transported to the light emitting layer, and can effectively trap a carrier and the leakage of an exciton, whereby an improvement in luminous efficiency and a reduction in voltage at which the device is driven can be achieved.

The term "hole transport region containing a compound represented by the general formula (1)" as used herein refers to a region for injecting/transporting mainly a hole such as the hole transport layer 5 described above.

It should be noted that the device constitutions shown in FIGS. 1, 2, 3 and 4 are merely very basic constitutions, and the constitution of an organic light emitting device using the compound of the present invention is not limited to these constitutions. The device may adopt any one of various layer constitutions. For example, an insulating layer may be provided onto an interface between an electrode and an organic layer. Alternatively, an adhesive layer or an interference layer may be provided.

The compound represented by the general formula (1) to be used in the present invention can be used in any one of the forms shown in FIGS. 1, 2, 3 and 4.

In particular, an organic layer using the compound of the present invention is useful as a light emitting layer or a hole injection/transport layer. In addition, a layer formed by, for example, a vacuum deposition method or a solution application method hardly undergoes, for example, crystallization, and is excellent in stability over time.

In the present invention, a compound represented by the general formula (1) is used particularly as a component of a light emitting layer; a conventionally known, low-molecular-weight-based or polymer-based hole transport compound, luminescent compound, electron transport compound, or the like can be used together with the compound as required.

A substrate to be used in the present invention is not particularly limited; provided that an opaque substrate such as a metallic substrate or a ceramic substrate, or a transparent substrate such as glass, quartz, or a plastic sheet is used.

In addition, a luminescent color can be controlled by using a color filter film, a fluorescent color conversion filter film, a dielectric reflective film, or the like as the substrate. Alternatively, a device can be produced by producing a thin film transistor (TFT) on a substrate and by connecting the TFT to the substrate.

In addition, with regard to the direction in which light is extracted from the device, both a bottom emission constitution (constitution in which light is extracted from a substrate side) and a top emission constitution (constitution in which light is extracted from the side opposite to the substrate) are available.

Hereinafter, the present invention will be described more specifically by way of examples. However, the present invention is not limited to these examples.

EXAMPLE 1

(Synthesis of Exemplified Compound 3)

a) Synthesis of Intermediate Compound 1-1

Intermediate was produced by using 2,7-ditertiarybutylfluorene (SIGMA-ALDRICH) as a raw material (Bull. Chem. Soc. Jpn., 59, 97-103 (1986)). Further, the intermediate was subjected to dimethylation to produce Intermediate 1-1.

b) Synthesis of Exemplified Compound 3

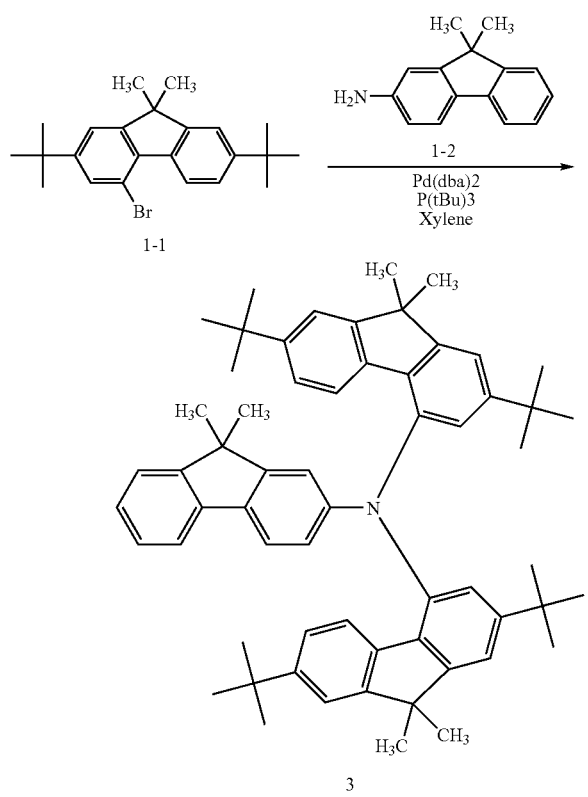

A 200-ml three-necked flask was prepared. 4.56 g (12.0 mmol) of Compound 1-1 were loaded into the flask. In addition, 0.828 g (4.00 mmol) of Compound 1-2 and 0.96 g (10.0 mmol) of sodium tertiary butoxide were loaded into the flask. Further, 100 ml of xylene were loaded into the flask, and then 34.4 mg (0.17 mmol) of tritertiarybutylphosphine were added while the mixture was stirred in a nitrogen atmosphere at room temperature. Next, 48.9 mg (0.085 mmol) of palladium dibenzylideneacetone were added. The temperature of the resultant was increased to 125° C., and then the resultant was stirred for 3 hours. After the reaction, an organic layer was extracted with toluene, dried with anhydrous sodium sulfate, and purified with a silica gel column (mixed developing solvent of heptane and toluene), whereby 2.53 g of Exemplified Compound 3 (white crystal) were obtained (78.0% yield).

Mass spectrometry confirmed that the M+ of the compound was 817.5. In addition, differential scanning calorimetry (DSC) confirmed that the compound had a melting point of 267° C. and a glass transition point of 143° C.

EXAMPLES 2 TO 11

(Synthesis of Exemplified Compounds 1, 2, 4, 8, 16, 17, 18, 27, 29, and 46)

Each of the compounds was synthesized in the same manner as in Example 1 except that a bromine body and an amino body shown in Table 1 below were used instead of Compounds 1-1 and 1-2.

TABLE 1

| Example | Exemplified Compound | Bromine body | Amino body |
|---|---|---|---|
| 2 | 1 | (structure) | (structure) |
| 3 | 2 | (structure) | (structure) |
| 4 | 4 | (structure) | (structure) |

TABLE 1-continued

| Example | Exemplified Compound | Bromine body | Amino body |
|---|---|---|---|
| 5 | 8 | | |
| 6 | 16 | | |
| 7 | 17 | | |
| 8 | 18 | | |
| 9 | 27 | | |
| 10 | 29 | | |

TABLE 1-continued

| Example | Exemplified Compound | Bromine body | Amino body |
|---|---|---|---|
| 11 | 46 | (9,9-dimethyl-fluoren-2-yl bromide) | (9,9-dimethyl-2,7-di-tert-butyl-fluorene with NH₂) |

EXAMPLES 12 TO 15

(Synthesis of Exemplified Compounds 51, 61, 62, and 68)

Each of the compounds was synthesized in the same manner as in Example 1 except that a bromine body and an amino body shown in Table 2 below were used instead of Compounds 1-1 and 1-2.

Mass spectrometry identified the structure of each of the compounds. In addition, Table 2 shows the glass transition temperature of each of the compounds measured by differential scanning calorimetry (DSC).

TABLE 2

| Example | Exemplified Compound | Bromine body | Amino Body | Grass transition Temperature (° C.) |
|---|---|---|---|---|
| 12 | 51 | | | 163 |
| 13 | 61 | | | 148 |
| 14 | 62 | | | 136 |

TABLE 2-continued

| Example | Exemplified Compound | Bromine body | Amino Body | Grass transition Temperature (° C.) |
|---|---|---|---|---|
| 15 | 68 | 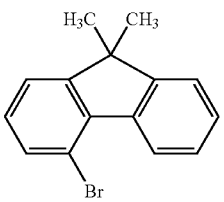 [SMILES: CC1(C)c2ccccc2-c2c(Br)cccc21] | 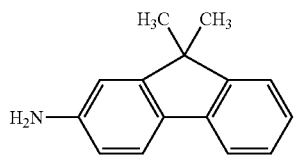 [SMILES: CC1(C)c2ccccc2-c2ccc(N)cc21] | 132 |

EXAMPLE 16

An organic light emitting device having a structure shown in FIG. 3 was produced by the following method.

Indium tin oxide (ITO) was formed by a sputtering method into a film having a thickness of 120 nm to serve as the anode 2 on a glass substrate as the substrate 1, and the resultant was used as a transparent, conductive supporting substrate. The substrate was subjected to ultrasonic cleaning with acetone and isopropyl alcohol (IPA) sequentially. Then, the substrate was subjected to boiling cleaning with IPA, followed by drying. Further, the substrate was subjected to UV/ozone cleaning. The resultant was used as a transparent, conductive supporting substrate.

Exemplified Compound 3 was formed by a vacuum deposition method into a film having a thickness of 20 nm to serve as the hole transport layer 5. The film was formed under conditions including: a degree of vacuum upon deposition of $1.0 \times 10^{-4}$ Pa; and a film formation rate of 0.1 nm/sec.

Next, Compound 2-1 shown below to serve as a light emitting layer was vapor-deposited onto the hole transport layer 5 to provide the light emitting layer 3 having a thickness of 20 nm. The layer was formed under conditions including: a degree of vacuum upon deposition of $1.0 \times 10^{-4}$ Pa; and a film formation rate of 0.1 nm/sec.

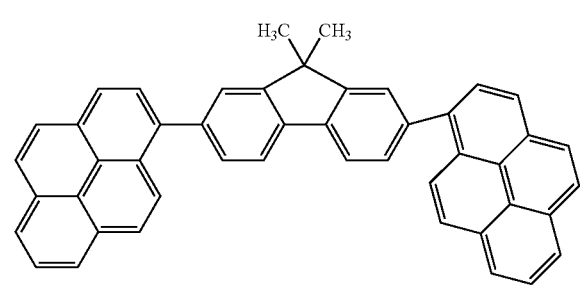

2-1

Further, bathophenanthroline (BPhen) was formed by a vacuum deposition method into a film having a thickness of 40 nm to serve as the electron transport layer 6. The film was formed under conditions including: a degree of vacuum upon deposition of $1.0 \times 10^{-4}$ Pa; and a film formation rate of 0.2 to 0.3 nm/sec.

Next, a metal layer film having a thickness of 0.5 nm was formed by a vacuum deposition method on the foregoing organic layer by using a deposition material composed of an aluminum-lithium alloy (having a lithium concentration of 1 atomic %). Further, an aluminum film having a thickness of 150 nm was provided by a vacuum deposition method. Thus, an organic light emitting device using the aluminum-lithium alloy film as an electron injection electrode (cathode 4) was produced. The films were each formed under conditions including: a degree of vacuum upon deposition of $1.0 \times 10^{-4}$ Pa; and a film formation rate of 1.0 to 1.2 nm/sec.

The resultant organic EL device was covered with a protective glass plate in a dry air atmosphere and sealed with an acrylic resin-based adhesive in order that the device might be prevented from deteriorating owing to the adsorption of moisture.

A voltage of 4.0 V was applied to the thus-obtained device by using the ITO electrode (anode 2) as a positive electrode and the Al electrode (cathode 4) as a negative electrode. As a result, the device was observed to emit blue light having an emission luminance of 3,045 cd/m$^2$ and a center wavelength of 462 nm.

Further, a voltage was applied while a current density was kept at 30 mA/cm$^2$ under a nitrogen atmosphere. As a result, the deterioration of luminance 100 hours after the application as compared to initial luminance was small.

EXAMPLES 17 TO 26

Devices were each produced in the same manner as in Example 16 except that a compound shown in Table 1 or Table 2 was used instead of Exemplified Compound 3 serving as the hole transport layer 3 of Example 16, and were each evaluated in the same manner as in Example 16. As a result, each of the devices was observed to emit light.

TABLE 3

| Example | Exemplified Compound No. |
|---|---|
| 17 | 1 |
| 18 | 2 |
| 19 | 4 |
| 20 | 8 |
| 21 | 18 |
| 22 | 46 |
| 23 | 51 |
| 24 | 61 |
| 25 | 62 |
| 26 | 68 |

COMPARATIVE EXAMPLES 1 AND 2

Devices were each produced in the same manner as in Example 16 except that Comparative Compound 4-1 or 4-2 shown below was used instead of Exemplified Compound 3, and were each evaluated in the same manner as in Example 16. As a result, none of the devices was observed to emit light.

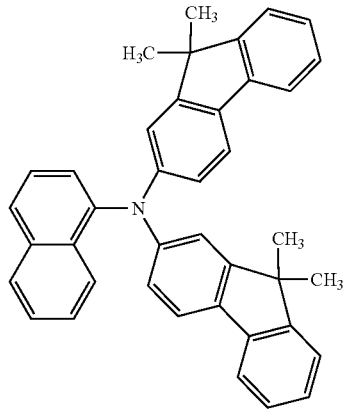

4-1

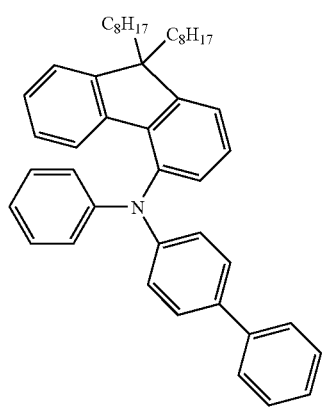

4-2

EXAMPLE 27

An organic light emitting device having a structure shown in FIG. 4 was produced by the following method.

Indium tin oxide (ITO) was formed by a sputtering method into a film having a thickness of 120 nm to serve as the anode 2 on a glass substrate as the substrate 1, and the resultant was used as a transparent, conductive supporting substrate. The substrate was subjected to ultrasonic cleaning with acetone and isopropyl alcohol (IPA) sequentially. Then, the substrate was subjected to boiling cleaning with IPA, followed by drying. Further, the substrate was subjected to UV/ozone cleaning. The resultant was used as a transparent, conductive supporting substrate.

A chloroform solution was prepared by using Exemplified Compound 1 in the first hole transport layer 5-1 in such a manner that the concentration of the compound would be 0.1 wt %.

The solution was dropped onto the above ITO electrode, and the whole was subjected to spin coating initially at a number of revolutions of 500 RPM for 10 seconds and then at a number of revolutions of 1,000 RPM for 1 minute, whereby a film was formed. After that, the resultant was dried for 10 minutes in a vacuum oven at 80° C., whereby the solvent in the thin film was completely removed. The first hole transport layer 5-1 thus formed had a thickness of 11 nm.

Next, Exemplified Compound 3 was vapor-deposited onto the first hole transport layer 5-1 to provide the electron hole transport layer 5-2 having a thickness of 20 nm. The layer was formed under conditions including: a degree of vacuum upon deposition of $1.0 \times 10^{-4}$ Pa; and a film formation rate of 0.1 nm/sec.

Further, a light emitting layer, an electron transport layer, and an Al electrode were each produced in the same manner as in Example 16.

A voltage of 4.0 V was applied to the thus-obtained device by using the ITO electrode (anode 2) as a positive electrode and the Al electrode (cathode 4) as a negative electrode. As a result, the device was observed to emit blue light having an emission luminance of 2,908 cd/m$^2$ and a center wavelength of 464 nm.

Further, a voltage was applied while a current density was kept at 30 mA/cm$^2$ under a nitrogen atmosphere. As a result, the deterioration of luminance 100 hours after the application as compared to initial luminance was small.

EXAMPLE 28

An organic light emitting device having a structure shown in FIG. 3 was produced by the following method.

Indium tin oxide (ITO) was formed by a sputtering method into a film having a thickness of 120 nm to serve as the anode 2 on a glass substrate as the substrate 1, and the resultant was used as a transparent, conductive supporting substrate. The substrate was subjected to ultrasonic cleaning with acetone and isopropyl alcohol (IPA) sequentially. Then, the substrate was subjected to boiling cleaning with IPA, followed by drying. Further, the substrate was subjected to UV/ozone cleaning. The resultant was used as a transparent, conductive supporting substrate.

A chloroform solution was prepared by using Exemplified Compound 8 in the hole transport layer 5 in such a manner that the concentration of the compound would be 0.1 wt %.

The solution was dropped onto the above ITO electrode, and the whole was subjected to spin coating initially at a number of revolutions of 500 RPM for 10 seconds and then at a number of revolutions of 1,000 RPM for 1 minute, whereby a film was formed. After that, the resultant was dried for 10 minutes in a vacuum oven at 80° C., whereby the solvent in the thin film was completely removed. The hole transport layer 5 thus formed had a thickness of 12 nm.

Next, Compound 5-1 and Compound 5-2 were subjected to co-deposition at a ratio of Compound 5-1 to Compound 5-2 of 5 wt %, whereby the light emitting layer 4 having a thickness of 25 nm was provided.

Further, an electron transport layer and an Al electrode were each produced in the same manner as in Example 16.

A voltage of 4.0 V was applied at a current density of 3.9 mA/cm$^2$ to the thus-obtained device by using the ITO electrode (anode 2) as a positive electrode and the Al electrode (cathode 4) as a negative electrode. As a result, the device was observed to emit blue light having an emission luminance of 408 cd/m$^2$.

Further, a voltage was applied while a current density was kept at 30 mA/cm$^2$ under a nitrogen atmosphere. As a result, the deterioration of luminance 100 hours after the application as compared to initial luminance was small.

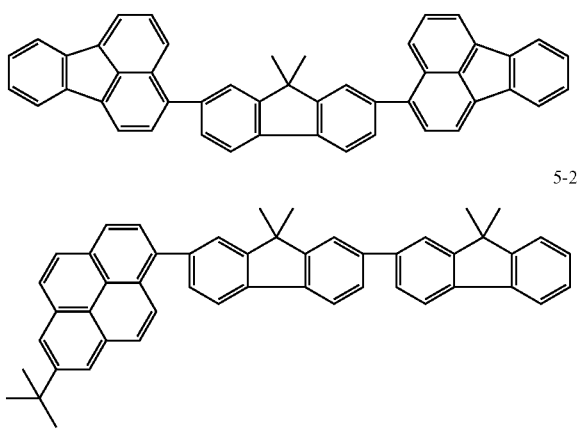

5-1

5-2

EXAMPLE 29

An organic light emitting device having a structure shown in FIG. 3 was produced by the following method.

Indium tin oxide (ITO) was formed by a sputtering method into a film having a thickness of 120 nm to serve as the anode 2 on a glass substrate as the substrate 1, and the resultant was used as a transparent, conductive supporting substrate. The substrate was subjected to ultrasonic cleaning with acetone and isopropyl alcohol (IPA) sequentially. Then, the substrate was subjected to boiling cleaning with IPA, followed by drying. Further, the substrate was subjected to UV/ozone cleaning. The resultant was used as a transparent, conductive supporting substrate.

A chloroform solution was prepared by using Exemplified Compound 3 in the hole transport layer 5 in such a manner that the concentration of the compound would be 0.1 wt %.

The solution was dropped onto the above ITO electrode, and the whole was subjected to spin coating initially at a number of revolutions of 500 RPM for 10 seconds and then at a number of revolutions of 1,000 RPM for 1 minute, whereby a film was formed. After that, the resultant was dried for 10 minutes in a vacuum oven at 80° C., whereby the solvent in the thin film was completely removed. The hole transport layer 5 thus formed had a thickness of 11 nm.

Next, Compound 5-1 and Compound 5-2 were subjected to co-deposition at a ratio of Compound 5-1 to Compound 5-2 of 5 wt %, whereby the light emitting layer 4 having a thickness of 25 nm was provided.

Further, an electron transport layer and an Al electrode were each produced in the same manner as in Example 16.

A voltage of 4.0 V was applied at a current density of 3.6 mA/cm² to the thus-obtained device by using the ITO electrode (anode 2) as a positive electrode and the Al electrode (cathode 4) as a negative electrode. As a result, the device was observed to emit blue light having an emission luminance of 425 cd/m².

Further, a voltage was applied while a current density was kept at 30 mA/cm² under a nitrogen atmosphere. As a result, the deterioration of luminance 100 hours after the application as compared to initial luminance was small.

EXAMPLE 30

An organic light emitting device having a structure shown in FIG. 4 was produced by the following method.

Indium tin oxide (ITO) was formed by a sputtering method into a film having a thickness of 120 nm to serve as the anode 2 on a glass substrate as the substrate 1, and the resultant was used as a transparent, conductive supporting substrate. The substrate was subjected to ultrasonic cleaning with acetone and isopropyl alcohol (IPA) sequentially. Then, the substrate was subjected to boiling cleaning with IPA, followed by drying. Further, the substrate was subjected to UV/ozone cleaning. The resultant was used as a transparent, conductive supporting substrate.

A chloroform solution was prepared by using Exemplified Compound 3 in the first hole transport layer 5-1 in such a manner that the concentration of the compound would be 0.1 wt %.

The solution was dropped onto the above ITO electrode, and the whole was subjected to spin coating initially at a number of revolutions of 500 RPM for 10 seconds and then at a number of revolutions of 1,000 RPM for 1 minute, whereby a film was formed. After that, the resultant was dried for 10 minutes in a vacuum oven at 80° C., whereby the solvent in the thin film was completely removed. The first hole transport layer 5-1 thus formed had a thickness of 12 nm.

Next, Exemplified Compound 8 was vapor-deposited onto the first hole transport layer 5-1 to provide the second hole transport layer 5-2 having a thickness of 20 nm. The layer was formed under conditions including: a degree of vacuum upon deposition of $1.0 \times 10^{-4}$ Pa; and a film formation rate of 0.1 nm/sec.

Next, Compound 5-1 and Compound 5-2 were subjected to co-deposition at a ratio of Compound 5-1 to Compound 5-2 of 5 wt %, whereby the light emitting layer 4 having a thickness of 25 nm was provided.

Further, an electron transport layer and an Al electrode were each produced in the same manner as in Example 16.

A voltage of 4.0 V was applied at a current density of 4.3 mA/cm² to the thus-obtained device by using the ITO electrode (anode 2) as a positive electrode and the Al electrode (cathode 4) as a negative electrode. As a result, the device was observed to emit blue light having an emission luminance of 523 cd/m². Here, the band gap of Compound 8 is larger than that of Compound 5-2. In addition, the ionization potential of Exemplified Compound 3 is deeper than the ionization potential of Exemplified Compound 8, and the ionization potential of Exemplified Compound 8 is deeper than the ionization potential of Exemplified Compound 5-2.

Further, a voltage was applied while a current density was kept at 30 mA/cm² under a nitrogen atmosphere. As a result, the deterioration of luminance 100 hours after the application as compared to initial luminance was small.

This application claims the benefit of Japanese Patent Application Nos. 2005-366558, filed Dec. 20, 2005, 2006-166200, filed Jun. 15, 2006 and 2006-315716, filed Nov. 22, 2006 which are hereby incorporated by reference herein in their entirety.

The invention claimed is:

1. A 4-aminofluorene compound represented by the following general formula (1):

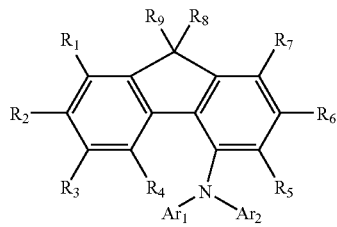

wherein Ar1 represents a substituted or unsubstituted fluorene group bonded at 2- or 4-position, Ar2 represents a substituted or unsubstituted aryl group or a substituted or unsubstituted heterocyclic group, and $R_1$ to $R_9$ each represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen group, and may be identical to or different from each other, or may be bonded to each other to form a ring.

2. The 4-aminofluorene compound according to claim 1, wherein in the general formula (1), Ar1 represents a substituted or unsubstituted fluorene group bonded at the 4-position.

3. The 4-aminofluorene compound according to claim 1, wherein in the general formula (1), Ar1 represents a substituted or unsubstituted fluorene group bonded at the 4-position, and Ar2 represents a substituted or unsubstituted fluorene group.

4. An organic light emitting device comprising:
a pair of electrodes composed of an anode and a cathode; and
plural layers each containing an organic compound, the plural layers being interposed between the pair of electrodes,
wherein the plural layers comprise:
a light emitting layer,
a second hole transport layer adjacent to the light emitting layer on the anode side of the light emitting layer, and
a first hole transport layer adjacent to the second hole transport layer on the anode side of the second hole transport layer, the first hole transport layer and the second hole transport layer containing the 4-aminofluorene compound according to claim 1,
wherein the 4-aminofluorene compound of the first hole transport layer and the 4-aminofluorene compound of the second hole transport layer are different from each other.

5. The organic light emitting device according to claim 4, wherein a band gap of the 4-aminofluorene compound present in the second hole transport layer is wider than a band gap of a compound a content of which in the light emitting layer is highest.

6. The organic light emitting device according to claim 4, wherein an ionization potential Ip1 of a compound a content of which in the first hole transport layer is highest, an ionization potential Ip2 of a compound a content of which in the second hole transport layer is highest, and an ionization potential Ip3 of a compound a content of which in the light emitting layer is highest satisfy a relationship of Ip1<Ip2<Ip3.

7. An organic light emitting device comprising:
a pair of electrodes composed of an anode and a cathode; and
a light emitting layer containing an organic compound and being interposed between the pair of electrodes,
wherein the light emitting layer containing an organic compound contains at least one kind of the compound according to claim 1.

8. An organic light emitting device comprising:
a pair of electrodes composed of an anode and a cathode; and
a layer comprising a light emitting layer and a hole transport layer, and being interposed between the pair of electrodes, the layer excluding another hole transport layer,
wherein the hole transport layer contains at least one kind of the compound according to claim 1.

9. An organic light emitting device comprising:
a pair of electrodes composed of an anode and a cathode; and
plural layers each containing an organic compound, the plural layers being interposed between the pair of electrodes,
wherein the plural layers comprise:
a light emitting layer,
a second hole transport layer adjacent to the light emitting layer on the anode side of the light emitting layer, and
a first hole transport layer adjacent to the second hole transport layer on the anode side of the second hole transport layer, the first hole transport layer containing the 4-aminofluorene compound according to claim 1.

10. An organic light emitting device comprising:
a pair of electrodes composed of an anode and a cathode; and
a layer containing an organic compound and being interposed between the pair of electrodes,
wherein the layer containing an organic compound contains at least one kind of the compound according to claim 1.

11. An apparatus comprising:
a substrate; and
the organic light emitting device according to claim 10.

12. The apparatus according to claim 11, further comprising a color filter.

13. An organic light emitting device comprising:
a pair of electrodes composed of an anode and a cathode; and
a layer containing an organic compound and being interposed between the pair of electrodes,
wherein the layer containing an organic compound is a hole transport region containing at least one kind of the compound according to claim 1.

14. An organic light emitting device comprising:
a pair of electrodes composed of an anode and a cathode; and
a layer containing an organic compound and being interposed between the pair of electrodes,
wherein the layer containing an organic compound is a light emitting layer containing at least one kind of the compound according to claim 1.

* * * * *